(12) United States Patent
Schmoyer

(10) Patent No.: US 11,787,995 B2
(45) Date of Patent: Oct. 17, 2023

(54) METHOD FOR EXTRACTING HYDROCARBONS

(71) Applicant: SO3 PLUS, LLC, Birmingham, MI (US)

(72) Inventor: Thomas Earl Schmoyer, Birmingham, MI (US)

(73) Assignee: SO3 PLUS, LLC, Birmingham, MI (US)

( * ) Notice: Subject to any disclaimer, the term of this patent is extended or adjusted under 35 U.S.C. 154(b) by 281 days.

(21) Appl. No.: 16/639,811

(22) PCT Filed: Aug. 20, 2018

(86) PCT No.: PCT/US2018/047028
§ 371 (c)(1),
(2) Date: Feb. 18, 2020

(87) PCT Pub. No.: WO2019/036698
PCT Pub. Date: Feb. 21, 2019

(65) Prior Publication Data
US 2021/0388254 A1    Dec. 16, 2021

Related U.S. Application Data

(60) Provisional application No. 62/547,577, filed on Aug. 18, 2017.

(51) Int. Cl.
*E21B 43/16*     (2006.01)
*C09K 8/52*      (2006.01)
*E21B 41/00*     (2006.01)
*C01B 17/74*     (2006.01)

(52) U.S. Cl.
CPC ............... *C09K 8/52* (2013.01); *C01B 17/74* (2013.01); *E21B 41/0099* (2020.05); *E21B 43/16* (2013.01); *C09K 2208/22* (2013.01)

(58) Field of Classification Search
CPC ....... C09K 8/52; E21B 41/0099; E21B 43/16; C01B 17/74
See application file for complete search history.

(56) References Cited

U.S. PATENT DOCUMENTS

| | | | |
|---|---|---|---|
| 2,817,635 A | 12/1957 | Goldman et al. |
| 2,818,079 A | 12/1957 | Garrison |
| 3,067,134 A | 12/1962 | Parks et al. |
| 3,162,601 A | 12/1964 | Jones |
| 3,244,188 A | 4/1966 | Parks et al. |

(Continued)

OTHER PUBLICATIONS

Charles, J.G., "Parrafin Inhibition Treatments Reduce Well Maintenance," SPE Paper 13362, Oct.-Nov. 1984, 6 pgs.

(Continued)

*Primary Examiner* — Silvana C Runyan
(74) *Attorney, Agent, or Firm* — Brooks Kushman P.C.

(57) ABSTRACT

Portable/transportable apparatuses, methods, and systems for generating and delivering sulfur trioxide on-site or near an item to be treated is provided. A method for extracting hydrocarbons from deposits containing a clathrate hydrate such as methane hydrates includes a step of delivering sulfur trioxide to an ice deposit containing a clathrate hydrate and subsequently extracting linear or branched hydrocarbons.

5 Claims, 14 Drawing Sheets

(56) References Cited

U.S. PATENT DOCUMENTS

| | | | |
|---|---|---|---|
| 3,693,720 | A | 9/1972 | McDougall et al. |
| 4,099,537 | A | 7/1978 | Kalfoglou et al. |
| 4,455,175 | A | 6/1984 | Settineri et al. |
| 4,536,222 | A | 8/1985 | Settineri et al. |
| 4,722,398 | A * | 2/1988 | Bohlen ............... C09K 8/524 134/29 |
| 6,572,835 | B1 | 6/2003 | MacArthur et al. |
| 6,602,326 | B2 | 8/2003 | Lee et al. |
| 6,733,573 | B2 | 5/2004 | Lyon |
| 6,758,910 | B2 | 7/2004 | Schmoyer |
| 6,855,852 | B1 * | 2/2005 | Jackson ............... C10L 3/108 585/15 |
| 7,282,603 | B2 | 10/2007 | Richards |
| 2004/0060438 | A1 * | 4/2004 | Lyon ............... C07C 7/00 95/153 |
| 2006/0251570 | A1 | 11/2006 | Smith et al. |
| 2008/0226540 | A1 * | 9/2008 | Felthouse ............ B01J 35/1009 423/538 |
| 2012/0067568 | A1 * | 3/2012 | Palmer ............... F23J 15/00 166/402 |

OTHER PUBLICATIONS

Charles, J.G., "Water-Wet Surfaces for Long-Term Paraffin Inhibition," SPE Paper 14520, Nov. 6-9, 1985, 9 pgs.

Hester, K.C. et al., "Clathrate Hydrates in Nature," Annual Review of Marine Science 1, 2009, pp. 303-327.

Mukhopadhyay, S. et al., "A High-Yield Approach to the Sulfonation of Methane to Methanesulfonic Acid Initiated by $H_2O_2$ and a Metal Chloride," Angewandte Chemie, v. 115, 2003, pp. 3098-3101.

International Search Report and Written Opinion dated Dec. 18, 2018 for PCT/US2018/047028 filed Aug. 20, 2018, 13 pgs.

* cited by examiner

METHOD FOR EXTRACTING HYDROCARBONS

CROSS-REFERENCE TO RELATED APPLICATIONS

This application is the U.S. national phase of PCT/US2018/047028 filed Aug. 20, 2018, which claims the benefit of U.S. provisional application Ser. No. 62/547,577, filed on 18 Aug. 2017, the disclosure of which is hereby incorporated in its entirety by reference herein.

BACKGROUND

References such as U.S. Pat. Nos. 4,455,175 and 4,536,222 issued to Dow Chemical Company and U.S. Pat. No. 4,722,398 issued to Dowell Schlumberger, which are all incorporated by reference, describe in detail the benefits of using sulfur trioxide and hydroxyl ions to remove and retard paraffins in crude oil and natural gas pipelines and equipment. These references fail to describe how sulfur trioxide is transported to the well site. Sulfur trioxide is normally transported as a solid and or liquid. The sulfur trioxide has a strong tendency to form high melting crystals below 90° F. (32.22° C.) and high temperatures and extended periods of time are required to liquefy the crystallized sulfur trioxide. Additional safety, liability and environmental concerns of sulfur trioxide in contact with moisture creating a thermal reaction and creation of sulfuric acid caused the technology to be abandoned.

Further, methane hydrates, also known as methane clathrate, methane clathrate hydrate, hydromethane, methane ice, fire ice, natural gas hydrate, gas hydratemethane clathrate, or flammable ice, are vast reservoirs of natural gas trapped in ice-like crystals and hold the potential to alter trade flows and reshape the geopolitics of energy. Methane hydrates are classified as a clathrate hydrate. Methane hydrates consist of a methane molecule surrounded by a cage of interlocking water molecules. Hydrates store large amounts of gas in a relatively small area; one cubic meter of hydrate can hold around 160 cubic meters of methane and 0.8 cubic meters of water. Methane hydrates are similar to ice in their composition and occur naturally in subsurface deposits in freezing temperature and high-pressure conditions. The sea floor is thus an ideal location for their formation: the deep seabed is uniformly cold, with temperatures from zero to four degrees Celsius, and below a water depth of about 350 meters, the pressure is sufficient to stabilize the hydrates. When melted or exposed to pressures and temperatures outside those where the ice is stable, the solid crystalline lattice turns into liquid water, and the enclosed methane molecules are released as gas. The implications of methane hydrates as a new energy source for countries lacking access to conventional resources are therefore profound. It is thought that methane hydrates may be able to supply the natural gas needs for a century. Domestically produced methane hydrate gas has the potential to reduce the dependence on imports that has defined its energy system throughout the modern era. Several technologies are being developed or have developed to produce or extract the methane hydrates. But using these technologies to produce or extract the methane hydrates or other clathrate hydrates are cost prohibitive.

The following references are incorporated by reference: U.S. Pat. Nos. 2,817,635, 2,818,079, 3,067,134, 3,162,601, 3,244,188, 3,693,720, 4,099,537, 4,455,175, 4,536,222, 4,722,398, and 6,733,573. The following publication are also incorporated by reference: (1) Paraffin Inhibition Treatments Reduce Well Maintenance, by J. G. Charles, SPE Paper 13362, October-November 1984 and (2) Water-Wet Surfaces for Long-Term Paraffin Inhibition, by J. G. Charles, SPE Paper 14520, Nov. 6-9, 1985.

The new process of the present application preferably does not require any transportation of sulfur trioxide as it is manufactured on demand at the well site or treatment location in small amounts. The new process is preferably safe, an automatically close system, and does not require any EPA permits.

While certain novel features of the present disclosure shown and described below are pointed out in the annexed claims, the present disclosure is not intended to be limited to the details specified, since a person of ordinary skill in the relevant art will understand that various omissions, modifications, substitutions and changes in the forms and details of the device illustrated and in its operation may be made without departing in any way from the spirit of the present disclosure. No feature of the disclosure is critical or essential unless it is expressly stated as being "critical" or "essential."

SUMMARY

The present disclosure, in general, relates to portable/transportable apparatuses, methods, and systems for generating and delivering sulfur trioxide on-site or near an item to be treated. The present disclosure also relates to portable/transportable apparatuses, methods, and systems for removing hydrocarbon contaminants including waxes, paraffins, resins, and ashpaltenes from surfaces and treating the surfaces to reduce hydrocarbon contaminant build-up on the surfaces. The present disclosure also relates to portable/transportable apparatuses, methods, and systems for extracting hydrocarbons from deposits containing a clathrate hydrate such as methane hydrate.

In various embodiments are disclosed transportable apparatuses/systems for on-demand sulfur trioxide generation, the transportable apparatus including: a sulfur trioxide generating system comprising portable sources of sulfur and oxygen; a converter having an inlet fluidly or gaseously coupled to the portable sources of sulfur and oxygen, a cavity communicating with the inlet and containing a catalyst capable of catalyzing a reaction of sulfur and oxygen to generate sulfur trioxide, and an outlet communicating with the cavity and capable of dispensing the generated sulfur trioxide; and a heater operable to heat sulfur or oxygen dispensed from the portable sources to a temperature sufficient for generating sulfur trioxide; and a transportable base adapted to support the sulfur trioxide generating system and is transportable to a site when supporting the sulfur trioxide generating system; wherein the sulfur trioxide generating system is operable to generate and dispense sulfur trioxide at the site. In various embodiments, the site is a plurality of sites and may include sites at or near a well-site, piping, transport line, equipment, fixtures, and storage containers. In various embodiments, the converter is a plurality of converters serially arranged and coupled fluidly or gaseously with each other. Also, the converter of various embodiments is thermally coupled to heater and/or is thermally insulated. In various embodiments, the transportable apparatus and/or sulfur trioxide generating system is maintained substantially always at a temperature of at least 50° F. (10° C.), 55° F. (12.78° C.), 60° F. (15.56° C.), 65° F. (18.33° C.), 70° F. (21.11° C.), 75° F. (23.89° C.), 80° F. (26.637° C.), 85° F. (29.44° C.), or 90° F. (32.22° C.). In various embodiments, the transportable apparatus and/or sulfur trioxide generating system is maintained substantially always at a temperature between two temperatures in this paragraph.

In various embodiments, the sulfur trioxide generating system is operable at the site to generate sulfur trioxide at a rate ranging from about 0.5 gallon (1.89 liters) to about 200 gallons (757.08 liters) per hour or at a rate ranging from about 1 fluid ounce (29.57 milliliters) to about 426.67 ounces (12.62 liters) per minute. Also, the sulfur trioxide generating system of various embodiments is operable at the site to adjust or maintain a pressure ranging from about 5 pounds per square inch (34.47 kilopascals) to about 5000 pounds per square inch (34,473.79 kilopascals).

In various embodiments, the base is a skid on which the portable sources of sulfur and oxygen. the converter, and heater are mounted on. The transportable base of various embodiments can have a length ranging from about 4 feet (121.92 centimeters) to about 48 feet (1463.04 centimeters) and a width ranging from about 3 feet (91.44 centimeters) to about 12 feet (365.76 centimeters).

In various embodiments, the sulfur trioxide generating system when adapted on the transportable base can be arranged to fit within a space a length ranging from about 4 feet (121.92 centimeters) to about 48 feet (1463.04 centimeters), a width ranging from about 3 feet (91.44 centimeters) to about 12 feet (365.76 centimeters), and a height ranging from about 4 feet (121.92 centimeters) to about 18 feet (548.64 centimeters).

In various embodiments, the transportable apparatus includes an enclosure substantially surrounding the base and sulfur trioxide generating system. The transportable base and enclosure of various embodiments together have a length ranging from about 4 feet (121.92 centimeters) to about 48 feet (1463.04 centimeters), a width ranging from about 3 feet (91.44 centimeters) to about 12 feet (365.76 centimeters), and a height ranging from about 4 feet (121.92 centimeters) to about 18 feet (548.64 centimeters).

In various embodiments, the portable source of sulfur is a pressurized source of liquid sulfur dioxide or raw sulfur and/or the portable source of oxygen is a pressurized source of liquid oxygen. The portable source of sulfur or oxygen of various embodiments is a storage container storing an amount of sulfur ranging from about 5 lbs. (2.27 kilograms) to about 2000 lbs. (907.18 kilograms) and can be thermally coupled to the heater and/or thermally insulated. The portable source of sulfur or oxygen of various embodiments can have a length ranging from about 1 feet (30.48 centimeters) to about 40 feet (15.24 meters), a width ranging from about 1 feet (30.48 centimeters) to about 8 feet (243.84 centimeters), and a height ranging from about 3 feet (91.44 centimeters) to about 12 feet (365.76 centimeters). Also, the portable source of sulfur or oxygen can have a diameter ranging from about 1 feet (30.48 centimeters) to about 40 feet (15.24 meters). Alternatively, the portable source of oxygen of various embodiments is an air compressor having a cubic feet per minute (CFM) rating of about 20 CFM (0.57 cubic meter per minute) to about 400 CFM (11.33 cubic meter per minute) and having a length ranging from about 3 feet (91.44 centimeters) to about 48 feet (1463.04 centimeters), a width ranging from about 3 feet (91.44 centimeters) to about 10 feet (304.8 centimeters), and a height ranging from about 3 feet (91.44 centimeters) to about 16 feet (487.68 centimeters).

In various embodiments, the converter is a sulfur dioxide to sulfur trioxide gas/liquid generator having a top, bottom, and side walls defining the cavity and the catalyst is positioned in a catalyst bed downstream of the inlet and upstream. The cavity of the sulfur dioxide to sulfur trioxide gas/liquid generator of various embodiments has a length ranging from about 24 inches (60.96 centimeters) to about 1440 inches (3657.6 centimeters), a width ranging from about 1 inches (2.54 centimeters) to about 72 inches (182.88 centimeters), and a height ranging from about 48 inches (121.92 centimeters) to about 192 inches (487.68 centimeters). Also, the sulfur dioxide to sulfur trioxide gas/liquid generator of various embodiments can further include a heat conducting element(s) positioned between the inlet and the catalyst bed and capable of heating the cavity or heating the sulfur and oxygen entering the generator through the inlet and/or a plurality of catalyst beds. The heat conducting element(s) of various embodiments is thermally coupled to the heat conducting element.

In various embodiments, the converter is a sulfur dioxide to sulfur trioxide gas/liquid isothermic converter having at least two generally straight piping sections and a pipe bend section arranged between the at least two generally straight piping sections and the piping sections each have a bore defining the cavity. The bore of various embodiments has a bore diameter ranging from about 1 inch (2.54 centimeters) to about 72 inches (182.88 centimeters) and the at least two generally straight piping sections of various embodiments has a length ranging from about 24 inches (60.96 centimeters) to about 480 inches (1219.2 centimeters). The pipe bend section of various embodiments has a curvature such that the at least two generally straight piping sections are positioned parallel to each other.

In various embodiments, the catalyst is a vanadium type catalyst that can have a curved shaped and can include vanadium oxide or vanadium pentoxide. In various embodiments, the amount of vanadium catalyst used for generating sulfur trioxide in the sulfur trioxide generating system ranges from about 5 lbs. (2.27 kilograms) to about 1000 lbs (453.6 kilograms).

In various embodiments, the heater is operable to heat sulfur or oxygen dispensed from the portable sources to a temperature of about 500° F. (260° C.) to about 2000° F. (1093.33° C.) and/or is operable to maintain the sulfur trioxide generating system at a temperature of at least 50° F. (10° C.). The heater of various embodiments has a length ranging from about 2 inches (5.08 centimeters) to about 480 inches (1219.2 centimeters), a width ranging from about 2 inches (5.08 centimeters) to about 72 inches (182.88 centimeters), and a height ranging from about 2 inches (5.08 centimeters) to about 480 inches (1219.2 centimeters).

In various embodiments, the transportable portable apparatus includes a scrubbing system supported by the transportable base and comprising a mist eliminator/scrubber fluidly or gaseously coupled to the outlet of the generator, a source of a neutralizing agent fluidly or gaseously coupled to the mist eliminator/scrubber, and a pump operable to recirculate the neutralizing agent between the mist eliminator/scrubber and the source of the neutralizing agent. The mist eliminator/scrubber of various embodiments has a length ranging from about 2 feet (60.96 centimeters) to about 24 feet (731.52 centimeters), a width ranging from about 2 feet (60.96 centimeters) to about 6 feet (182.88 centimeters), and a height ranging from about 3 feet (91.44 centimeters) to about 24 feet (731.52 centimeters). The mist eliminator/scrubber of various embodiments also has an inlet for receiving gases and a fiberbed membrane containing the neutralizing agent capable of reacting with sulfur trioxide and dissolving acids.

In various embodiments, the sulfur trioxide generating system includes a portable source of a flushing/pressure maintaining liquid or gas fluidly or gaseously coupled to the inlet of the generator that can be a storage container storing an amount of the flushing/pressure maintaining liquid or gas ranging from about 5 lbs. (2.27 kilograms) to about 1000 lbs (453.6 kilograms). The portable source of the flushing/pressure maintaining liquid or gas of various embodiments is pressurized liquid nitrogen and/or dry air. The portable source of flushing/pressure maintaining liquid or gas of various embodiments can have a length ranging from about 3 feet (91.44 centimeters) to about 48 feet (1463.04 centimeters), a width ranging from about 2 feet (60.96 centimeters) to about 12 feet (365.76 centimeters), and a height ranging from about 3 feet (91.44 centimeters) to about 16 feet (487.68 centimeters). Also, the portable source of flushing/pressure maintaining liquid or gas can have a diameter ranging from about 1 feet (30.48 centimeters) to about 40 feet (15.24 meters). Also, the portable source of flushing/pressure liquid or gas of various embodiments is thermally coupled to heater and/or thermally insulated.

In various embodiments, the sulfur trioxide generating system includes a plurality of conduits coupling components fluidly or gaseously together. The plurality of conduits of various embodiments are thermally insulated and/or thermally coupled to the heater. In one embodiment, one of the plurality of conduits fluidly or gaseously connects the portable source of oxygen to the converter. In another embodiment, one of the plurality of conduits fluidly or gaseously connects the portable source of sulfur to the converter. In one embodiment, one of the plurality of conduits is a discharge conduit fluidly or gaseously connecting the outlet of the converter and extending to the site.

In various embodiments, the sulfur trioxide generating system includes a humidity removal element capable of removing humidity from the portable sources of sulfur and/or oxygen. The humidity removal element of various embodiments includes a dessicant dryer.

In various embodiments, the sulfur trioxide generating system includes a sensor or a plurality of sensors including, for example, various indicators, transmitters, recorders, controllers, elements, gauges, transducers and alarms that are coupled to various components of the sulfur trioxide generating system. The indicators of various embodiments include, for example, temperature indicators, flow indicators, pressure indicators, and level indicators operable to acquire information when the sulfur trioxide generating system or any system of the present is in operation. The transmitters of various embodiments include, for example, temperature transmitters, flow transmitters, pressure transmitters, analyzer transmitters, and level transmitters operable to transmit the information. The recorders of various embodiments include, for example, temperature recorders, flow recorders, pressure recorders, and level recorders operable to record the information. The controllers of various embodiments include, for example, temperature controllers, flow controllers, pressure controllers, level controllers, pressure indicating controllers, and pressure recording controllers operable to control operation of the sulfur trioxide generating system or any system of any embodiment. The elements of various embodiments, include, for example, flow elements and temperature elements operable to provide output that can got to a controller. The gauge of various embodiments, include, for example, temperature gauges, flow gauges, pressure gauges, and level gauges capable of display information when the sulfur trioxide generating system or any system of any embodiment is in operation. The alarms of various embodiments include, for example, temperature alarms, flow alarms, pressure alarms, and level alarms capable of alerting a user when the sulfur trioxide generating system or any system of any embodiment is not operating in a pre-determined manner.

In various embodiments, the sulfur trioxide generating system includes a valve or a plurality of valves coupled to the various components of the sulfur trioxide generating system and operable to regulates, directs or control the flow of a fluid by opening, closing, or partially obstructing passageways. The valves of various embodiments can include rotameters, orifices, and other types of valves.

In various embodiments, the sulfur trioxide generating system includes a main controller coupled to receive information from the plurality of sensors, having a display for the received information, and operable to engage and control the plurality of controllers.

In various embodiments, the sulfur trioxide generating system includes a sulfur trioxide cooler fluidly or gaseously coupled to the outlet and capable of cooling the sulfur trioxide to a liquid and separating oxygen from the generated sulfur trioxide.

In various embodiments, the sulfur trioxide generating system includes a mist eliminator/oleum separator coupled to the sulfur trioxide cooler and capable of separating oleum form the generated sulfur trioxide.

In various embodiments, the apparatus includes an electrical generator supported by the transportable base and operable to provide electricity to the sulfur trioxide generating system as well as the apparatus.

In various embodiments, the apparatus includes a space heater supported by the transportable base and operable to maintain the sulfur trioxide generating system at a temperature of at least about 50° F. (10° C.).

In various embodiments, the apparatus includes a vehicle operable to transport the transportable base supporting the sulfur trioxide generating system to the site.

In various embodiments are disclosed apparatus, systems, and methods for removing hydrocarbon contaminants build-up on and treating surfaces of a drill string or wellbore and including: a sulfur trioxide generating system; and a neutralizing system having a portable source of a neutralizing agent, a conduit coupled to the portable source of the neutralizing agent, and a pump operable to pump the neutralizing agent from the portable source and through the conduit; a transportable base adapted to support the sulfur trioxide generating and neutralizing systems and is transportable to a site when supporting the sulfur trioxide generating and neutralizing system; wherein the sulfur trioxide generating is operable to generate and dispense sulfur trioxide and neutralizing system is operable to dispense the neutralizing agent at the site.

In various embodiments, the portable source of a neutralizing agent includes portable sources of a caustic agent, positive ion neutralizing fluid/gas, water, or mixtures thereof. The caustic agent or positive ion neutralizing fluid/gas of various embodiments is sodium hydroxide or a solution of sodium hydroxide. The portable source of the neutralizing agent of various embodiments is a storage container or bag storing an amount of agent ranging from about 5 lbs. (2.27 kilograms) to about 5000 lbs. (2267.96 kilograms). The portable source of the neutralizing agent of various embodiments has a length ranging from about 2 feet (60.96 centimeters) to about 16 feet (487.68 centimeters), a width ranging from about 2 feet (60.96 centimeters) to about 16 feet (487.68 centimeters), and a height ranging from about 2 feet (60.96 centimeters) to about 24 feet (731.52 centimeters) or a diameter ranging from about 1 feet (30.48 centimeters) to about 40 feet (15.24 meters).

In various embodiments are disclosed apparatus, systems, and methods for removing hydrocarbon contaminants buildup on and treating surfaces of a drill string or wellbore and including: portable sources of sulfur, oxygen, and a neutralizing agent; and a converter fluidly or gaseously coupled to the portable sources of sulfur and oxygen and capable of catalyzing a reaction to generate sulfur trioxide from the sulfur and oxygen; wherein sulfur and oxygen are dispensed from the portable sources to generate sulfur trioxide; wherein the generated sulfur trioxide is delivered to a drill string and wellbore to remove hydrocarbon contaminates such as waxes, paraffins, resins, and ashpaltenes from the surfaces of the drill string and well bore; wherein after the sulfur trioxide is delivered to the drill string and well bore, the neutralizing agent is delivered to a site to treat surfaces; wherein the portable system has dimensions allowing for transport to the site and is operable to generate and dispense sulfur trioxide at the site.

In various embodiments are disclosed methods for extracting hydrocarbons including the steps of generating sulfur trioxide at or near a well-site of a deposit containing a clathrate hydrate, delivering the sulfur trioxide to the deposit where the sulfur trioxide reacts with the clathrate hydrate to generate a hydrocarbon, and recovering the hydrocarbon. The sulfur trioxide of various embodiments is prepared by combining a stream of sulfur with a stream of oxygen or air containing oxygen and catalyzing a reaction of the sulfur and oxygen in the combined stream and/or is generated at a rate of about 0.5 gallons (1.89 liters) per hour to about 2000 gallons (7570.82 liters) per hour. The hydrocarbon of various embodiments is a hydrocarbon gas such as methane, ethane, butane, propane, or mixtures thereof.

In various embodiments, the delivering step includes maintaining the sulfur trioxide substantially always at a temperature of at least 50° F. (10° C.) or at a temperature where the sulfur trioxide does not crystalize.

In various embodiments, the generated sulfur trioxide is combined a medium including, for example, nitrogen or air that is delivered to the deposit. The medium of various embodiments can be a gas or liquid. The medium of various embodiments can also be pressurized for delivery to the deposit.

The sulfur trioxide of various embodiments can also react with the clathrate hydrate or water to produce sulfuric acid, heat, and sulfonated derivatives such as alkylsulfonic acids, alkyl alcohols, or alkyl esters of the sulfonic acids.

Examples of sulfonated derivatives includes a compound of formula (I),

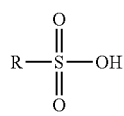

(I)

wherein R is linear or branched alkyl group with 1, 2, 3, 4 carbon atoms, or combinations thereof and the method further comprises the step of recovering the compound of formula (I) such as, for example, methane and sulfonic acid ($CH_6O_4S$).

In various embodiments, the methods further includes providing a transportable system for on-demand sulfur trioxide generation at or near a well-site of a deposit containing a clathrate hydrate, the transportable system having a portable source of sulfur, a portable source of oxygen or air containing oxygen, and a converter fluidly or gaseously coupled to the portable source of sulfur and the portable source of oxygen or air and capable of catalyzing a reaction to generate sulfur trioxide from the sulfur and oxygen, wherein sulfur and oxygen are dispensed from the portable sources to generate sulfur trioxide and the transportable system has dimensions allowing for transport to or near the well-site.

In various embodiments, the methods further include the step of extracting the linear or branched alkyl group from the compound of formula (I) and/or capturing the compound of formula (I).

In various embodiments are disclosed methods of extracting hydrocarbons comprising the steps of delivering sulfur trioxide, as a liquid or gas, to a deposit containing a clathrate hydrate, where at least the sulfur trioxide reacts with the clathrate hydrate to produce a sulfonated derivative such as alkylsulfonic acids, alkyl alcohols, alkyl esters of the sulfonic acids, or a compound of formula (I),

(I)

wherein R is linear or branched alkyl group with 1, 2, 3, 4 carbon atoms, or combinations thereof; and recovering the compound of formula (I). The reaction on various embodiments can also produce sulfuric acid or heat.

In various embodiments, the clathrate hydrate is a methane clathrate hydrate, ethane clathrate hydrate propane clathrate hydrate, butane clathrate hydrate, or combinations thereof.

BRIEF DESCRIPTION OF THE DRAWINGS

For a further understanding of the nature, objects, and advantages of the present disclosure, reference should be had to the following detailed description, read in conjunction with the following drawings, wherein like reference numerals denote like elements and wherein:

FIG. 2A also shows an apparatus and system of various embodiments mounted on a transportable base and substantially enclosed by an enclosure with a cross-sectional view of the conduits with are thermally coupled to the heater and are thermally insulated.

DETAILED DESCRIPTION

Figure 1:
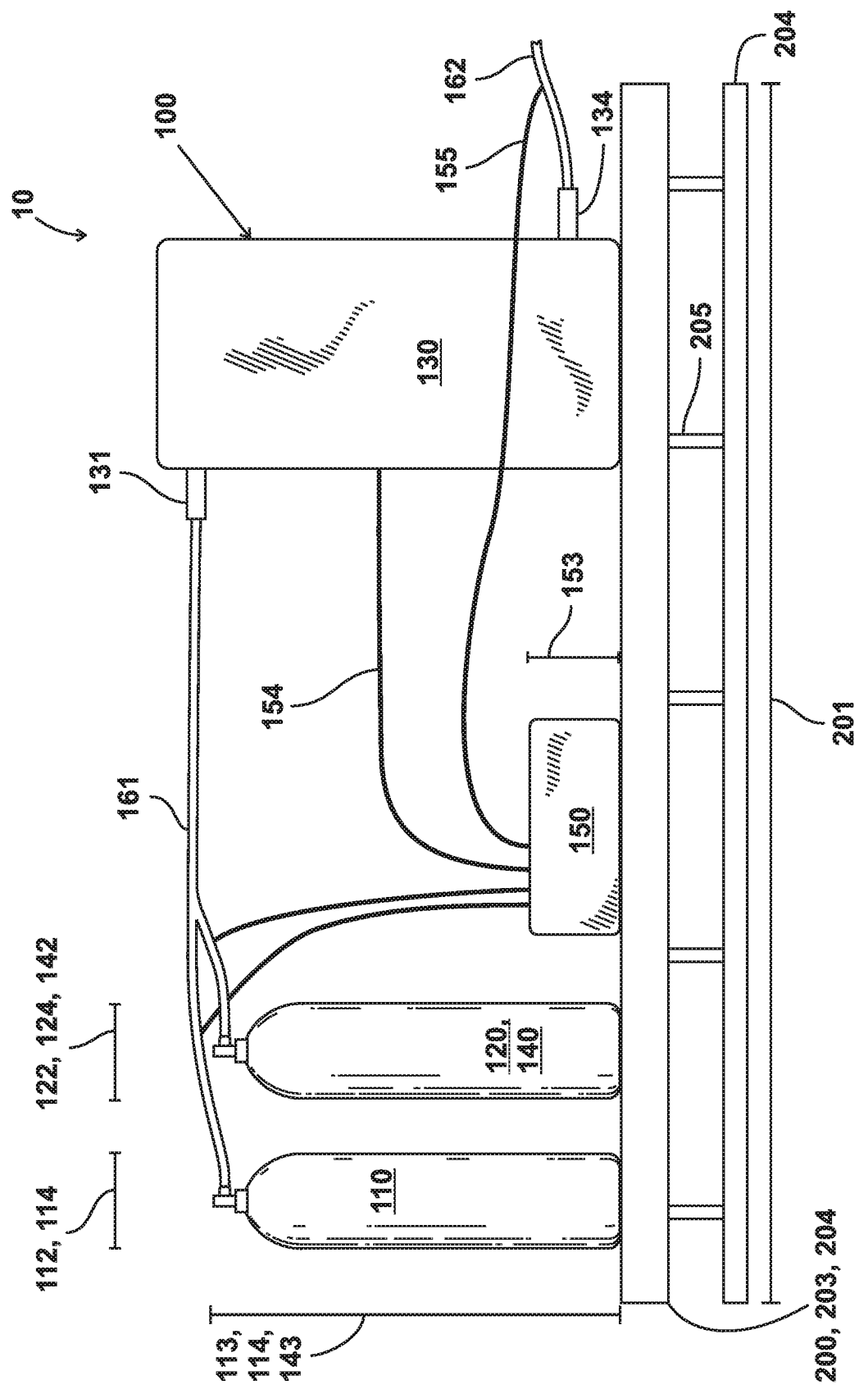
FIG. 1 shows an apparatus and system of various embodiments mounted on a transportable base such as a skid.
Figure 2A:
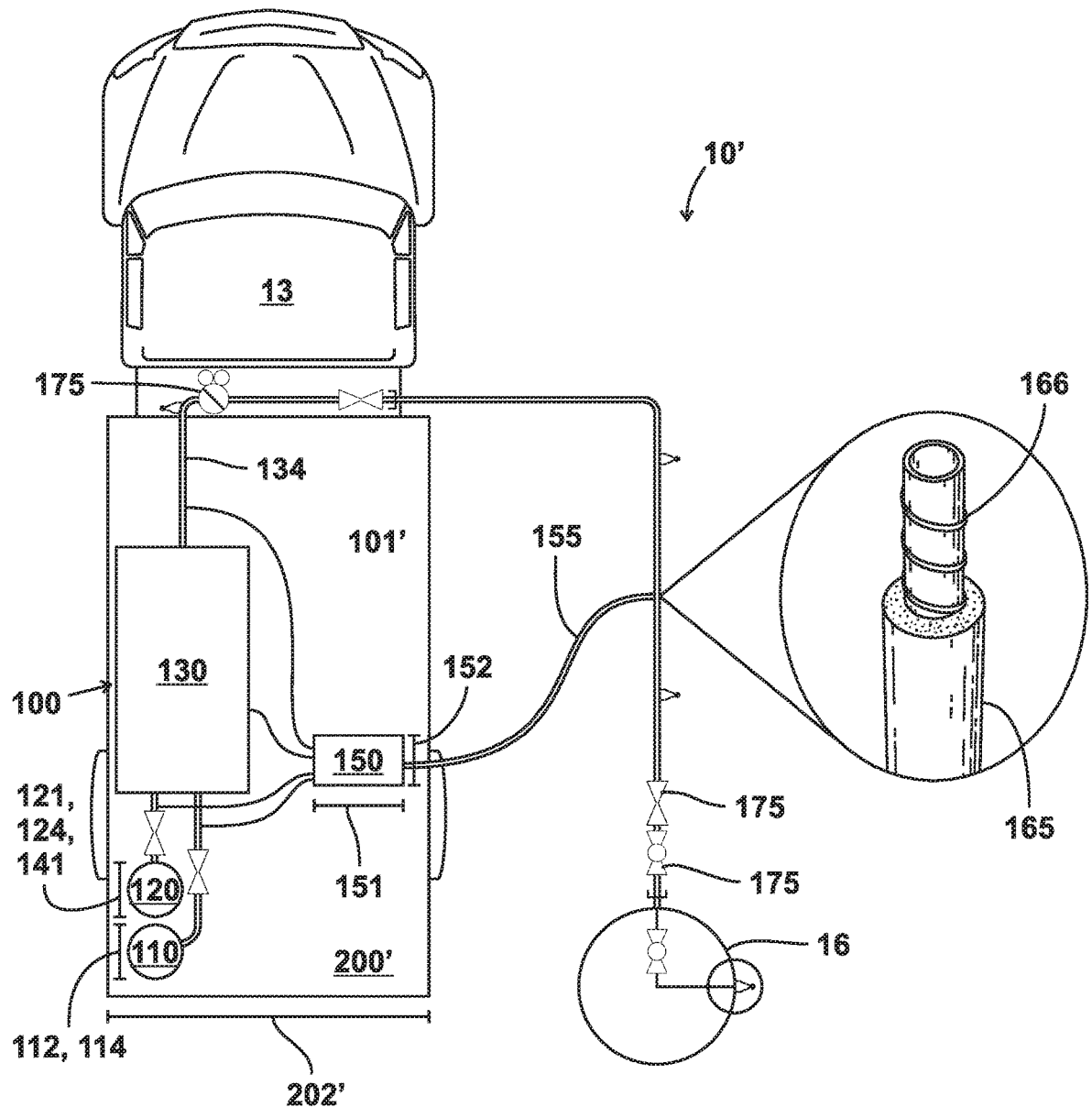
FIGS. 2A and 2B show an apparatus and system of various embodiments mounted on a transportable base and substantially enclosed by an enclosure, where the transportable base is capable of transport with a vehicle.
Figure 2B:
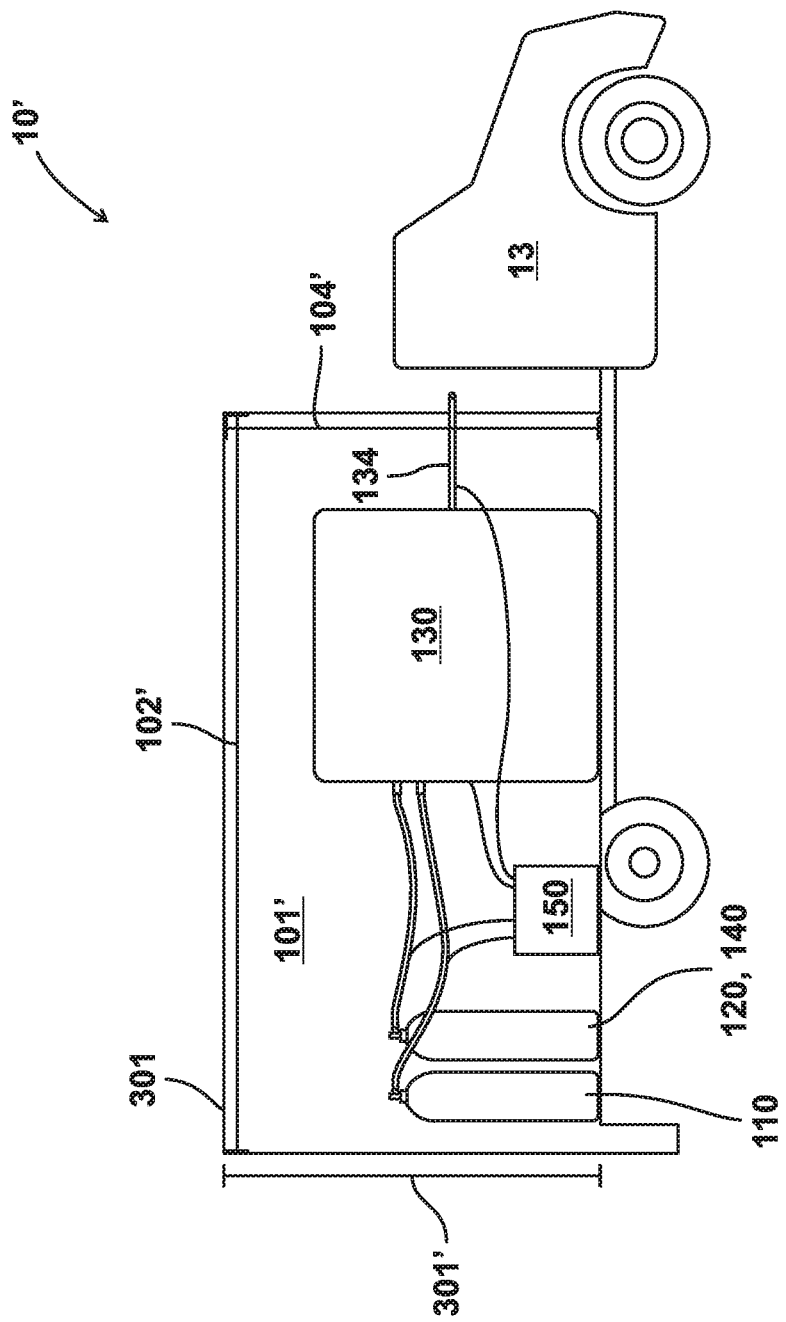

As required, detailed embodiments of the present disclosure are disclosed herein; however, it is to be understood that the disclosed embodiments are merely exemplary and may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art.

Except in the examples, or where otherwise expressly indicated, all numerical quantities in this description indicating amounts of material or conditions of reaction and/or use are to be understood as modified by the word "about". The first definition of an acronym or other abbreviation applies to all subsequent uses herein of the same abbreviation and applies mutatis mutandis to normal grammatical variations of the initially defined abbreviation; and, unless expressly stated to the contrary, measurement of a property is determined by the same technique as previously or later referenced for the same property.

Unless indicated otherwise, all technical and scientific terms used herein have the same meaning as commonly understood by one of ordinary skill in the art to which the present disclosure belongs. Also and unless indicated otherwise, all technical and scientific terms used herein have the meaning according to IUPAC convention.

It is also to be understood that this disclosure is not limited to the specific embodiments and methods described below, as specific components and/or conditions may, of course, vary. Furthermore, the terminology used herein is used only for describing particular embodiments and is not intended to be limiting in any way.

It is also noted that, as used in the specification and the appended claims, the singular form "a," "an," and "the" comprise plural referents unless the context clearly indicates otherwise. For example, reference to a component in the singular is intended to comprise a plurality of components.

The term "or" can be understood to mean "at least one of". The term "and" can also be understood to mean "at least one of" or "all".

The term "comprising" is synonymous with "including," "having," "containing," or "characterized by." These terms are inclusive and open-ended and do not exclude additional, unrecited elements or method steps.

The phrase "consisting of" excludes any element, step, or ingredient not specified in the claim. When this phrase appears in a clause of the body of a claim, rather than immediately following the preamble, it limits only the element set forth in that clause; other elements are not excluded from the claim as a whole.

The phrase "consisting essentially of" limits the scope of a claim to the specified materials or steps, plus those that do not materially affect the basic and novel characteristic(s) of the claimed subject matter.

The terms "comprising", "consisting of", and "consisting essentially of" can be alternatively used. When one of these three terms is used, the presently disclosed and claimed subject matter can include the use of either of the other two terms.

Unless expressly stated to the contrary: all R groups (e.g. $R_i$ where i is an integer) include H or hydrogen, alkyl, lower alkyl, $C_{1-6}$ alkyl, $C_{6-10}$ aryl, or $C_{6-10}$ heteroaryl; single letters (e.g., "n" or "o") are 1, 2, 3, 4, or 5; percent, "parts of," and ratio values are by weight; the description of a group or class of materials as suitable or preferred for a given purpose in connection with the disclosure implies that mixtures of any two or more of the members of the group or class are equally suitable or preferred; description of constituents in chemical terms refers to the constituents at the time of addition to any combination specified in the description, and does not necessarily preclude chemical interactions among the constituents of a mixture once mixed; the first definition of an acronym or other abbreviation applies to all subsequent uses herein of the same abbreviation and applies mutatis mutandis to normal grammatical variations of the initially defined abbreviation; and, unless expressly stated to the contrary, measurement of a property is determined by the same technique as previously or later referenced for the same property.

The term "alkyl" as used herein means $C_{1-20}$, linear, branched, rings, saturated or at least partially and in some cases fully unsaturated (i.e., alkenyl and alkynyl) hydrocarbon chains, including for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, butynyl, pentynyl, hexynyl, heptynyl, and allenyl groups. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. Lower alkyl can also refer to a range between any two numbers of carbon atoms listed above. "Higher alkyl" refers to an alkyl group having about 10 to about 20 carbon atoms, e.g., 10, 11, 12, 13, 14, 15, 16, 17, 18, 19, or 20 carbon atoms. Higher alkyl can also refer to a range between any two number of carbon atoms listed above. A saturated hydrocarbon refers to a hydrocarbon containing single bonds whereas, an unsaturated hydrocarbon refers to a hydrocarbon containing one or more double or triple bonds. Examples of alkyl groups include but are not limited to methyl, ethyl, propyl, isopropyl, butyl, isobutyl, sec-butyl, tert-butyl, pentyl, hexyl, octyl, ethenyl, propenyl, butenyl, pentenyl, hexenyl, octenyl, butadienyl, propynyl, butynyl, pentynyl, hexynyl, and allenyl groups. An alkyl group may also include cycloalkyl groups such as cyclopropyl, cyclopentyl, or cyclohexyl. Alkyl is intended to include isomers and enantiomers thereof. Examples of isomers include structural isomers or geometric isomers. The compounds disclosed herein may be prepared as a single isomer or as a mixture of isomers. Unless indicated otherwise a compound should be understood to comprise a mixture of the isomers. An alkyl group may be substituted with multiple substituent groups. For example, a substituent group may be but is not limited to a halogen, a hydroxyl, an alkoxy, an acetyl, phenyl, or amino group.

The term "aryl" as used herein means an aromatic substituent that can be a single aromatic ring, or multiple aromatic rings that are fused together, linked covalently, or linked to a common group, such as, but not limited to, a methylene or ethylene moiety. The common linking group also can be a carbonyl, as in benzophenone, or oxygen, as in diphenylether. Examples of aryl include, but are not limited to, phenyl, naphthyl, biphenyl, and diphenylether, and the like. Aryl groups include heteroaryl groups, wherein the aromatic ring or rings include a heteroatom (e.g., N, O, S, or Se). Exemplary heteroaryl groups include, but are not limited to, furanyl, pyridyl, pyrimidinyl, imidazoyl, benzimidazolyl, benzofuranyl, benzothiophenyl, quinolinyl, isoquinolinyl, thiophenyl, and the like. The aryl group can be optionally substituted (a "substituted aryl") with one or more aryl group substituents, which can be the same or different, wherein "aryl group substituent" includes alkyl (saturated or unsaturated), substituted alkyl (e.g., haloalkyl and perhaloalkyl, such as but not limited to —CF$_3$), cycloalkyl, aryl, substituted aryl, aralkyl, halo, nitro, hydroxyl, acyl, carboxyl, alkoxyl (e.g., methoxy), aryloxyl, aralkyloxyl, thioalkyl, thioaryl, thioaralkyl, amino (e.g., aminoalkyl, aminodialkyl, aminoaryl, etc.), sulfonyl, and sulfinyl.

The term "clathrate hydrate(s)" or "gas hydrate(s)" is used interchangeably to identify an ice-like crystalline form of water and low molecular weight gas (e.g., methane, ethane, propane, butane). Examples of clathrate hydrates can include various structures such as Structure I/Type 1 Clathrate Hydrate with hydrocarbons such as methane or ethane trapped within dodecahedron, hexakaidecahedron, or tetrakaidecaherdron water/ice cages; Structure II/Type II clathrate hydrates with hydrocarbons such as methane, ethane, propane, or butane trapped within hexakaidecahedron or tetrakaidecaherdron water/ice cages; or Structure H clathrate hydrates with hydrocarbons such as methane, ethane, propane, or butane trapped within water/ice cages. An example of a clathrate hydrate includes methane clathrate hydrate, ethane clathrate hydrate propane clathrate hydrate, or butane clathrate hydrate.

The term "methane hydrate(s)" and "methane clathrate hydrate(s)" can be used interchangeably to identify methane hydrates, methane clathrate, methane clathrate hydrate, hydromethane, methane ice, fire ice, natural gas hydrate, gas hydratemethane clathrate, or flammable ice.

The term "hydrocarbon sulfonic acid" can be used interchangeably to identify methane sulfonic acid, ethane sulfonic acid, propane sulfonic acid, butane sulfonic acid, or combinations thereof.

The present disclosure, in general, relates to portable/transportable apparatuses, methods, and systems for generating and delivering sulfur trioxide on-site or near an item to be treated. The present disclosure also relates to portable/transportable apparatuses, methods, and systems for removing hydrocarbon contaminants including paraffin and ashpaltenes from surfaces and treating the surfaces to reduce hydrocarbon contaminant build-up on the surfaces. The present disclosure as disclosed in various embodiments discloses improved method for treating crude oil and natural gas equipment surfaces to remove, inhibit and retard paraffins on equipment surfaces. The equipment surfaces include such equipment as pipelines both metal and polymeric, pumping equipment, valving, metering, transport lines, storage vessels and transport units.

FIGS. 1, 2A-2B, 5A-5B, and 7 show an apparatus and system of various embodiments. FIGS. 1, 2A-2B, 5A-5B, and 7 show a transportable apparatus 10, 10', 10", 10''' for on-demand sulfur trioxide includes sulfur trioxide generating system 100, 100", 100''' and a transportable base 200, 200', 200", 200''' adapted to support the sulfur trioxide generating system 100, 100", 100''' and is transportable to a site 16 when supporting the sulfur trioxide generating system. The apparatus 10, 10', 10", 10''' could be transported to a site 16 such as a wellsite or treatment location on a flatbed, cargo hauler or a vehicle such 13 as a cargo truck. The transportable apparatus 10 is also shippable to via a shipping container to a remote well location or an offshore well platform shown. FIGS. 1, 2A-2B, 5A-5B, and 6 show the apparatus 10', 10", 10' being capable of transport by a cargo truck 13. The apparatus 10, 10', 10", 10''' preferably eliminates the need to transport sulfur trioxide on the roadways or other means of transportation.

The transportable base 200, 200', 200", 200''' is adapted to support the sulfur trioxide generating system 100, 100", 100''' can have a length 201, 201', 201", 201' ranging from about 4 feet (121.92 centimeters) to about 48 feet (1463.04 centimeters) and a width 202, 202', 202", 202''' ranging from about 3 feet (91.44 centimeters) to about 12 feet (365.76 centimeters). In various embodiments, the length 201 and/or width 202 is 4 ft. (121.92 cm.); 5 ft. (152.4 cm.); 6 ft. (182.88 cm.); 7 ft. (213.36 cm.); 8 ft. (243.84 cm.); 9 ft. (274.32 cm.); 10 ft. (304.8 cm.); 10 ft. (304.8 cm.); 11 ft. (335.28 cm.); 12 ft. (365.76 cm.); 13 ft. (396.24 cm.); 14 ft. (426.72 cm.); 15 ft. (457.2 cm.); 16 ft. (487.68 cm.); 17 ft. (518.16 cm.); 18 ft. (548.64 cm.); 20 ft. (609.6 cm.); 25 ft. (762 cm.); 30 ft. (914.4 cm.); 35 ft. (1066.8 cm.); 40 ft. (1219.2 cm.); 45 ft. (1371.6 cm.); and 48 ft. (1463.04 cm.). In various embodiments, the length 201, 201', 201", 201' or width 202, 202', 202", 202''' can be between any two lengths or widths in this paragraph.

The transportable base 200 can be a skid 203 having a plurality of base members 204 supported by a plurality of support members 205 that allows a vehicle (i.e. a lift truck) to transport the apparatus 100.

The transportable apparatus 10, 10', 10", 10''' can also include an enclosure 300, 300', 300", 300''' that substantially surrounding the base and sulfur trioxide generating system 100, 100", 100'''. The enclosure 300, 300', 300", 300''' has matching dimensions with the transportable base 200, 200', 200", 200''' and can be thermally insulated. Also, the enclosure 300, 300', 300", 300''' has a height 301, 301', 301", 301''' of 4 ft. (121.92 cm.); 5 ft. (152.4 cm.); 6 ft. (182.88 cm.); 7 ft. (213.36 cm.); 8 ft. (243.84 cm.); 9 ft. (274.32 cm.); 10 ft. (304.8 cm.); 11 ft. (335.28 cm.); 12 ft. (365.76 cm.); 13 ft. (396.24 cm.); 14 ft. (426.72 cm.); 15 ft. (457.2 cm.); 16 ft. (487.68 cm.); 17 ft. (518.16 cm.); and 18 ft. (548.64 cm.). In various embodiments, the height 301, 301', 301", 301''' of the enclosure 300, 300', 300", 300''' can be between any two heights in this paragraph.

The sulfur trioxide generating system 100, 100", 100''' includes portable sources of sulfur 110 and oxygen 120; a converter having an inlet 131 fluidly or gaseously coupled to the portable sources of sulfur 110 and oxygen 120, a cavity 132 communicating with the inlet 131 and containing a catalyst 133 capable of catalyzing a reaction of sulfur and oxygen to generate sulfur trioxide, and an outlet 134 communicating with the cavity 132 and capable of dispensing the generated sulfur trioxide; and a heater 150 operable to heat sulfur or oxygen dispensed from the portable sources to a temperature sufficient for generating sulfur trioxide.

In various embodiments, the sulfur trioxide generating system 100, 100", 100''' when adapted on the transportable base 200, 200', 200", 200''' can be arranged to fit within a space 101', 101", 101''' having a length 102', 102", 102''', width 103', 103", 103''', and/or height width 104', 104", 104''' of 4 ft. (121.92 cm.); 5 ft. (152.4 cm.); 6 ft. (182.88 cm.); 7 ft. (213.36 cm.); 8 ft. (243.84 cm.); 9 ft. (274.32 cm.); 10 ft. (304.8 cm.); 10 ft. (304.8 cm.); 11 ft. (335.28 cm.); 12 ft. (365.76 cm.); 13 ft. (396.24 cm.); 14 ft. (426.72 cm.); 15 ft. (457.2 cm.); 16 ft. (487.68 cm.); 17 ft. (518.16 cm.); 18 ft. (548.64 cm.); 20 ft. (609.6 cm.); 25 ft. (762 cm.); 30 ft. (914.4 cm.); 35 ft. (1066.8 cm.); 40 ft. (1219.2 cm.); 45 ft. (1371.6 cm.); and 48 ft. (1463.04 cm.). In various embodiments, the length 102', 102", 102''', width 103', 103", 103', or height width 104', 104", 104''' can be between any two lengths, widths, or heights in this paragraph.

In various embodiments, the sulfur trioxide generating system 100, 100", 100''' is operable to generate sulfur trioxide at a rate ranging from about 0.5 gallon (1.89 liters) to about 200 gallons (757.08 liters) per hour. In various embodiments, the sulfur trioxide generating system 100 generates sulfur trioxide at a rate ranging from about 1 fluid ounce (29.57 milliliters) to about 426.67 ounces (12.62 liters) per minute. The portable apparatus of various embodiments can generate sulfur trioxide at a rate of 0.5 Gal. (1.89 L.), 1 Gal. (3.79 L.), 5 Gal. (18.93 L.), 10 Gal. (37.85 L.), 20 Gal. (75.71 L.), 30 Gal. (113.56 L.), 40 Gal. (151.42 L.), 50 Gal. (189.27 L.), 60 Gal. (227.12 L.), 70 Gal. (264.98 L.), 80 Gal. (302.83 L.), 90 Gal. (340.69 L.), 100 Gal. (378.54 L.), 110 Gal. (416.40 L.), 120 Gal. (454.25 L.), 130 Gal. (492.10 L.), 140 Gal. (529.96 L.), 150 Gal. (567.81 L.), 160 Gal. (605.67 L.), 170 Gal. (643.52 L.), 180 Gal. (681.37 L.), 190 Gal. (719.23 L.), 200 Gal. (757.08 L.); 300 Gal. (1135.62 L.); 400 Gal. (1514.16 L.); 500 Gal. (1892.71 L.); 600 Gal. (2271.25 L.); 700 Gal. (2649.79 L.); 800 Gal. (3028.33 L.); 900 Gal. (3406.87 L.); 1000 Gal. (3785.41 L.); 1100 Gal. (4163.95 L.); 1200 Gal. (4542.49 L.); 1300 Gal. (4921.04 L.); 1400 Gal. (5299.58 L.); 1500 Gal. (5678.12 L.); 1600 Gal. (6056.66 L.); 1700 Gal. (6435.20 L.); 1800 Gal. (6813.74 L.); 1900 Gal. (7192.28 L.); and 2000 Gal. (7570.82 L.) per hour. Alternatively, the sulfur trioxide generating system 100 generates sulfur trioxide at a rate of 1 fl. oz. (29.57 ml.), 10 fl. oz. (295.74 ml.), 50 fl. oz. (1478.68 ml.), 100 fl. oz. (2.96 L.), 150 fl. oz. (4.44 L.), 200 fl. oz. (5.91 L.), 250 fl. oz. (7.39 L.), 300 fl. oz. (8.87 L.), 350 fl. oz. (10.35 L.), 400 fl. oz. (11.83 L.), and 426.67 fl. oz. (12.62 L.) per minute. In various embodiments, the sulfur trioxide generating system 100, 100", 100''' is operable to generate sulfur trioxide at rate between any two rates in this paragraph.

In various embodiments, the sulfur trioxide generating system 100, 100", 100''' generates sulfur trioxide that is substantially pure. In various embodiments, the sulfur trioxide generating system 100, 100", 100''' generates sulfur trioxide at a theoretical rate of about 50%, 50.5%, 51%, 51.5%, 52%, 52.5%, 53%, 53.5%, 54%, 54.5%, 55%, 55.5%, 56%, 56.5%, 57%, 57.5%, 58%, 58.5%, 59%, 59.5%, 60%, 60.5%, 61%, 61.5%, 62%, 62.5%, 63%, 63.5%, 64%, 64.5%, 65%, 65.5%, 66%, 66.5%, 67%, 67.5%, 68%, 68.5%, 69%, 69.5%, 70%, 70.5%, 71%, 71.5%, 72%, 72.5%, 73%, 73.5%, 74%, 74.5%, 75%, 75.5%, 76%, 76.5%, 77%, 77.5%, 78%, 78.5%, 79%, 79.5%, 80%, 80.5%, 81%, 81.5%, 82%, 82.5%, 83%, 83.5%, 84%, 84.5%, 85%, 85.5%, 86%, 86.5%, 87%, 87.5%, 88%, 88.5%, 89%, 89.5%, 90%, 90.5%, 91%, 91.5%, 92%, 92.5%, 93%, 93.5%, 94%, 94.5%, 95%, 95.5%, 96%, 96.5%, 97%, 97.5%, 98%, 98.5%, 99%, 99.5%, and 100%. In other embodiments, the theoretical rate is 2%, 2.5%, 3%, 3.5%, 4%, 4.5%, 5%, 5.5%, 6%, 6.5%, 7%, 7.5%, 8%, 8.5%, 9%, 9.5%, 10%, 10.5%, 11%, 11.5%, 12%, 12.5%, 13%, 13.5%, 14%, 14.5%, 15%, 15.5%, 16%, 16.5%, 17%, 17.5%, 18%, 18.5%, 19%, 19.5%, 20%, 20.5%, 21%, 21.5%, 22%, 22.5%, 23%, 23.5%, 24%, 24.5%, 25%, 25.5%, 26%, 26.5%, 27%, 27.5%, 28%, 28.5%, 29%, 29.5%, 30%, 30.5%, 31%, 31.5%, 32%, 32.5%, 33%, 33.5%, 34%, 34.5%, 35%, 35.5%, 36%, 36.5%, 37%, 37.5%, 38%, 38.5%, 39%, 39.5%, 40%, 40.5%, 41%, 41.5%, 42%, 42.5%, 43%, 43.5%, 44%, 44.5%, 45%, 45.5%, 46%, 46.5%, 47%, 47.5%, 48%, 48.5%, 49%, and 49.5%. In various embodiments, the theoretical rate is between any two percentages in this paragraph.

In various embodiments, the transportable apparatus 10, 10', 10", 10''' and/or sulfur trioxide generating system 100, 100", 100''' is maintained substantially always at a temperature of at least 50° F. (10° C.), 55° F. (12.78° C.), 60° F. (15.56° C.), 65° F. (18.33° C.), 70° F. (21.11° C.), 75° F. (23.89° C.), 80° F. (26.637° C.), 85° F. (29.44° C.), or 90° F. (32.22° C.). In various embodiments, the transportable apparatus 10,10',10",10''' and sulfur trioxide generating system 100, 100", 100''' is maintained substantially always at a temperature between any two temperatures in this paragraph. In other embodiments, the transportable apparatus 10, 10', 10", 10''' and/or sulfur trioxide generating system 100, 100", 100''' is maintained at a temperature between any two temperatures in this paragraph. By maintaining the transportable apparatus 10, 10', 10", 10''' and/or sulfur trioxide generating system 100, 100", 100''' at these temperature, crystallization of the sulfur trioxide within the sulfur trioxide generating system 100, 100", 100''' is preferably limited and more preferably prevented.

In various embodiments, the sulfur trioxide generating system 100, 100",100''' is operable at the site to adjust or maintain the pressure to about 5 psi (34.47 kPa); 6 psi (41.67 kPa); 7 psi (48.26 kPa); 8 psi (55.16 kPa); 9 psi (62.05 kPa); 10 psi (68.95 kPa); 50 psi (344.74 kPa); 100 psi (689.48 kPa); 500 psi (3447.38 kPa); 1000 psi (6894.76 kPa); 1500 psi (10342.14 kPa); 2000 psi (13789.51 kPa); 2500 psi (17236.89 kPa); 3000 psi (20684.27 kPa); 3500 psi (24131.65 kPa); 4000 psi (27579.03 kPa); 4500 psi (31026.41 kPa); and 5000 psi (34473.79 kPa). In various embodiments, the sulfur trioxide generating system 100 is operable to adjust or maintain a pressure between any two pressures in this paragraph.

In one embodiment, the mobile unit 10, 10', 10", 10''', 100, 100", 100''' is capable of making sulfur trioxide liquid and/or gas on demand at the treatment location, the wellsite or location to treat tubing, transport lines, storage tanks and containers, pipe and additional equipment. The on-demand sulfur trioxide generating apparatus/system 10, 10', 10", 10''', 100, 100", 100''' can preferably generate ~5-10 gallons (18.93 liters ~37.85 liters) of sulfur trioxide at a preferable rate of ~1 to 5 ounces (29.57 milliliters-147.87 milliliters) of sulfur trioxide per minute or 600 gallons (2271.25 liters) per hour. This unit 10, 10', 10", 10''', 100, 100", 100''' preferably eliminates the need to transport sulfur trioxide on the roadways or other means of transportation.

The sulfur trioxide generating system 100, 100", 100''' includes portable sources of sulfur 110 and oxygen 120. In various embodiment for generating sulfur trioxide. The portable sources of sulfur 110 and oxygen 120 dispense sulfur and oxygen to the convert 130. In various embodiments, the portable sources of sulfur 110 and oxygen 120 can include pressurized sources of sulfur dioxide and oxygen.

In one example, sulfur dioxide is supplied as a liquid in pressurized cylinders. The sulfur dioxide in the cylinders can be heated to a cylinder temperature of 125° F. (51.67° C.) to build the sulfur dioxide supply pressure and vaporize the sulfur dioxide. In the example, the nominal cylinder pressure is 95 psig (655 kpa) at 115° F. (46.11° F.). The sulfur dioxide supply pressure of the example is a let-down in pressure using a relieving regulator to supply oxygen to the process. The node in this example can go from the cylinders to the isolation solenoids. In one example, about 0.5 moles of oxygen are used per mole of sulfur dioxide reacted. In the example of methods of various embodiments to produce 8.0 Lbs/Hr (3.63 kg/hr) of sulfur trioxide can use about 6.8 Lbs/Hr (3.08 kk/hr) of sulfur dioxide and 1.8 Lbs/Hr (0.82 kg/hr) of oxygen.

In another example, oxygen is preferably supplied from high pressure compressed gas cylinders. The oxygen pressure is preferably let-down in pressure using relieving regulator to supply oxygen to the process. The node of the example goes from the cylinders to isolation solenoids. In various embodiments, methods of producing sulfur trioxide preferably can include using about 0.5 moles of oxygen used per mole of sulfur dioxide reacted. In various embodiments, the molar ratio of sulfur dioxide to oxygen used to generate sulfur trioxide is 0.5, 1, 1.5, 2, 2.5 3, 3.5, 4, 4.5, 5, 5.5, 6, 6.5, 7, 7.5, 8, 8.5, 9, 9.5, and 10. In various embodiments, the molar ratio of sulfur dioxide used to oxygen used to generate sulfur trioxide is between any two molar ratios in the paragraph. For example to produce 8.0 Lbs/Hr (3.63 kg/hr) of sulfur trioxide, used about 6.8 Lbs/Hr (3.08 kg/hr) of sulfur dioxide, and 1.8 Lbs/Hr (0.82 kg/hr) of oxygen. In various embodiments, ratio of rates (lbs/hr or kg/hr) of sulfur dioxide to oxygen dispensed to generate sulfur trioxide is 0.5, 1, 1.5, 2, 2.5 3, 3.5, 3.78, 4, 4.5, 5, 5.5, 6, 6.5, 7, 7.5, 8, 8.5, 9, 9.5, and 10. In various embodiments, ratio of rates (lbs/hr or kg/hr) of sulfur dioxide to oxygen dispensed to generate sulfur trioxide is between any two rates in this paragraph, The portable sources of sulfur 110 and oxygen 120 includes is a storage container storing sulfur or oxygen in an amount of 5 lbs. (2.27 kg.); 6 lbs. (2.72 kg.); 7 lbs. (3.18 kg.); 8 lbs. (3.63 kg.); 9 lbs. (4.08 kg.); 10 lbs. (4.54 kg.); 50 lbs. (22.68 kg.); 100 lbs. (45.36 kg.); 500 lbs. (226.80 kg.); 1000 lbs. (453.59 kg.); 1500 lbs. (680.39 kg.); and 2000 lbs. (907.18 kg.). In various embodiments, the portable sources of sulfur 110 and oxygen 120 stores an amount of sulfur or oxygen between any two amounts in this paragraph. The portable sources of sulfur 110 and oxygen 120 of various embodiments has a length 112,122, width 113,123, height 111,121, and/or diameter 114, 124 of 1 ft. (30.48 cm.); 2 ft. (60.96 cm.); 3 ft. (91.44 cm.); 4 ft. (121.92 cm.); 5 ft. (152.40 cm.); 6 ft. (182.88 cm.); 7 ft. (213.36 cm.); 8 ft. (243.84 cm.); 9 ft. (274.32 cm.); 10 ft. (304.80 cm.); 11 ft. (335.28 cm.); 12 ft. (365.76 cm.); 15 ft. (457.20 cm.); 20 ft. (609.60 cm.); 25 ft. (762.00 cm.); 30 ft. (914.40 cm.); 35 ft. (1066.80 cm.); and 40 ft. (1219.20 cm.). In various embodiments, the length 112,122, width 113,123, height 111,121, and/or diameter 114, 124 of the portable sources of sulfur 110 and oxygen 120 is between any two lengths, widths, heights, and/or diameters in this paragraph.

In various embodiments, the portable source of oxygen 120 is liquid or gas oxygen. In these embodiments, the portable source of oxygen 120 being liquid or gas oxygen preferably allows for the generation of sulfur trioxide that is substantially free of oxygen outside of/not including the oxygen from the sulfur trioxide that can include, for example, various oxygen species (i.e. 02) and radicals. In various, embodiments, the portable source of oxygen 120 being liquid or gas oxygen allows for the generation of sulfur trioxide having a reduced oxygen content, where the reduced oxygen content is outside of/not including the oxygen from the sulfur trioxide. In other embodiments, the portable source of oxygen 120 being liquid or gas oxygen more preferably allows for the generation of sulfur trioxide that is free of oxygen outside of/not including the oxygen from the sulfur trioxide.

Alternatively, the portable sources of oxygen is an air compressor 140 having a cubic feet per minute (CFM) rating of 20 CFM (0.57 cubic meter per minute); 30 CFM (0.89 cubic meter per minute); 40 CFM (1.13 cubic meter per minute); 50 CFM (1.42 cubic meter per minute); 60 CFM (1.70 cubic meter per minute); 70 CFM (1.98 cubic meter per minute); 80 CFM (2.27 cubic meter per minute); 90 CFM (2.55 cubic meter per minute); 100 CFM (2.83 cubic meter per minute); 150 CFM (4.25 cubic meter per minute); 200 CFM (5.66 cubic meter per minute); 250 CFM (7.08 cubic meter per minute); 300 CFM (8.50 cubic meter per minute); 350 CFM (9.91 cubic meter per minute); and 400 CFM (11.32 cubic meter per minute). In various embodiments, the air compressor 140 has a cubic feet per minute (CFM) rating between any two ratings in this paragraph. Also, the air compressor 140 of various embodiments has a length 142, width 143, and height 144 of 3 ft. (91.44 cm.); 4 ft. (121.92 cm.); 5 ft. (152.40 cm.); 6 ft. (182.88 cm.); 7 ft. (213.36 cm.); 8 ft. (243.84 cm.); 9 ft. (274.32 cm.); 10 ft. (304.80 cm.); 15 ft. (457.20 cm.); 20 ft. (609.60 cm.); 25 ft. (762.00 cm.); 30 ft. (914.40 cm.); 35 ft. (1066.80 cm.); 40 ft. (1219.20 cm.); 45 ft. (1371.60 cm.); and 48 ft. (1463.04 cm.). In various embodiments, the length 122', width 123', and height 121' of the air compressor 120' are between any two lengths, widths, heights, and/or diameters in this paragraph.

In various examples, the mobile apparatus/systems include a number of distinct process operations as shown in the Figures. In one example, liquid sulfur dioxide flows from a dip tube type storage cylinder and is vaporized and regulated to the correct flow rate and pressure. The vaporized sulfur dioxide is introduced into the inlet of a converter.

In various examples, liquid oxygen is stored in a dewar cylinder and is vaporized and regulated to the correct flow and pressure. In one example, the vaporized oxygen is introduced to the converter at the correct volume and pressure. In another example, dry air may be substituted for the oxygen but results in a non-oxygen free sulfur trioxide.

Figure 6:
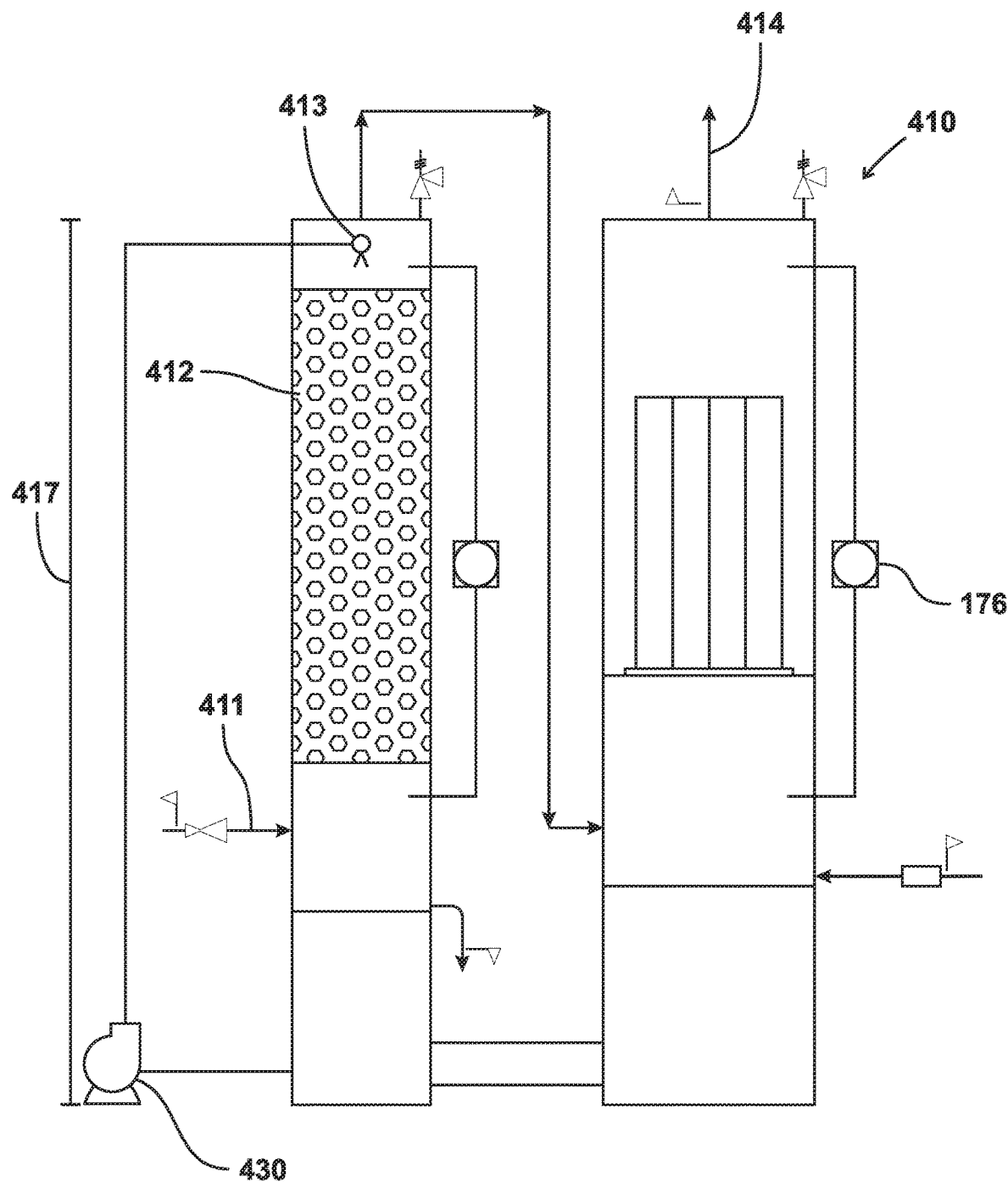
FIG. 6 shows a mist eliminator/scrubber of various embodiments.

The converter 130 preferably receives sulfur and oxygen from the portable sources sulfur 110 and oxygen 120 and generates sulfur trioxide from the sulfur and oxygen. The converter 130 preferably includes a catalyst 133 located within the cavity 132 and is heated to a temperature a temperature of about 500° F. (260° C.) to about 2000° F. (1093.33° C.) to convert the sulfur and oxygen to sulfur trioxide. In various embodiments, the converter 130 is similar to converters produced in sold by Chemithon Corporation of Seattle, Wash., as a flue gas conditioning system as highlight disclosed in U.S. Pat. Nos. 6,758,910 and 6,572,835, which are incorporated by reference as well as converters produced and sold by Environment Equipment Services of Knoxville, Tenn. In various embodiments, the sulfur trioxide generating system 100, 100",100''' includes 2, 3, 4, 5, 6, 7, 8, 9, 10 converters that are arranged serially or in parallel. In various embodiments, the sulfur trioxide generating system 100, 100", 100''' has a number of converters 130 between any number of converters 130 in this paragraph. Also, the converter 130 as shown in FIG. 6 can be enclosed in a container 135 to preferably maintain the converter at a temperature sufficient for generating sulfur trioxide In various embodiments, the catalyst 133 in the cavity 132 is a vanadium type catalyst that can have a curved shaped and can include vanadium oxide or vanadium pentoxide. In various embodiments, the amount of vanadium catalyst 133 used for generating sulfur trioxide in the sulfur trioxide generating system 100, 100", 100''' ranges from about 5 lbs. (2.27 kilograms) to about 1000 lbs (453.6 kilograms). In various embodiments, the amount of catalyst in the cavity is 5 lbs. (2.27 kg.); 6 lbs. (15.24 kg.); 7 lbs. (17.78 kg.); 8 lbs. (20.32 kg.); 9 lbs. (22.86 kg.); 10 lbs. (25.40 kg.); 50 lbs. (127.00 kg.); 100 lbs. (254.00 kg.); 200 lbs. (508.00 kg.); 300 lbs. (762.00 kg.); 400 lbs. (1016.00 kg.); 500 lbs. (1270.00 kg.); 600 lbs. (1524.00 kg.); 700 lbs. (1778.00 kg.); 800 lbs. (2032.00 kg.); 900 lbs. (2286.00 kg.); 1000 lbs. (2540.00 kg.). In various embodiments, the amount is catalyst in the cavity is between any amount in the paragraph.

Figure 3:
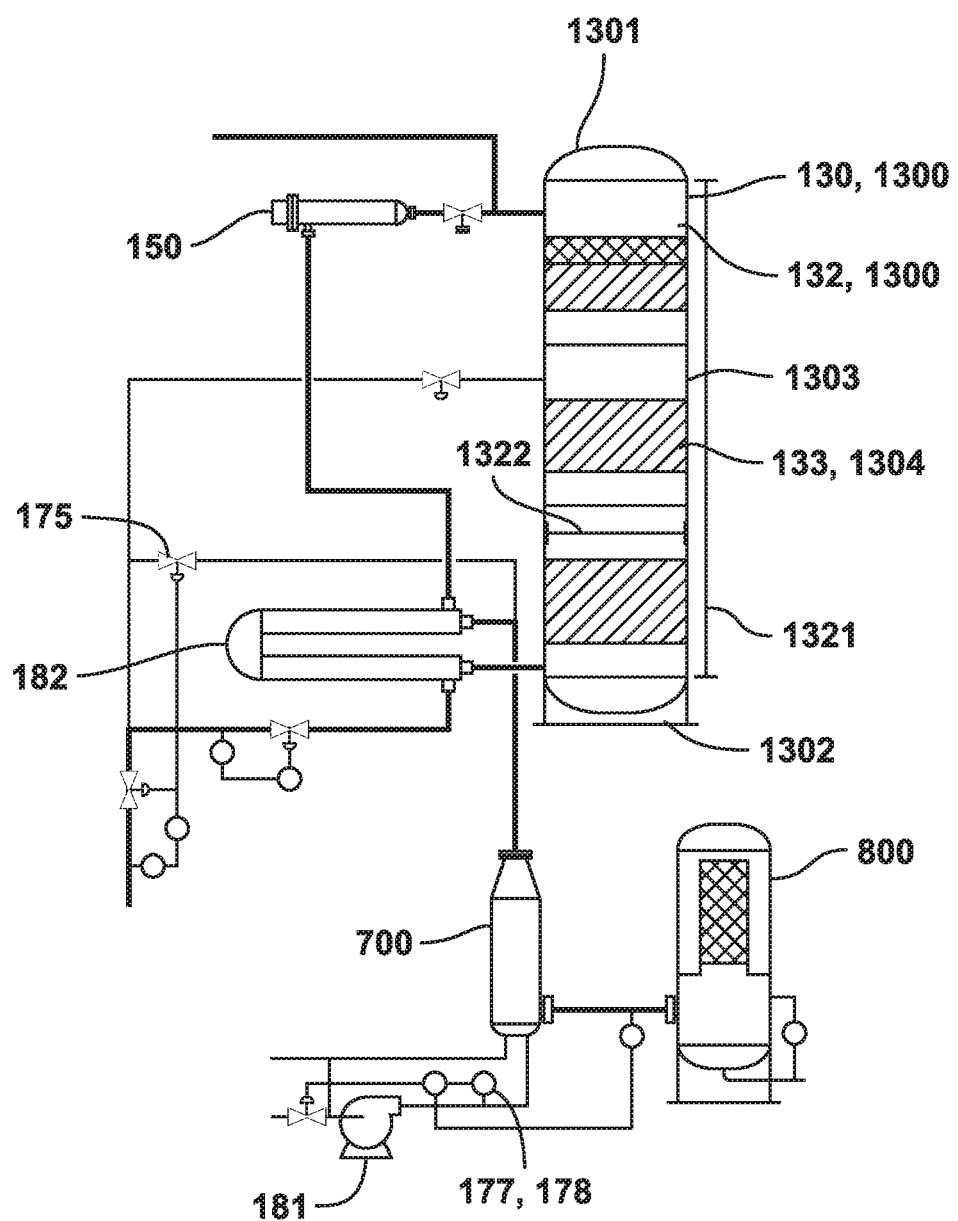
FIGS. 3 and 4 show piping diagrams of various embodiments.

As shown in FIG. 3, the converter 130 is a sulfur dioxide to sulfur trioxide gas/liquid generator 1300 having a top 1301, bottom 1302, and side walls 1303 defining a cavity 1320 and the catalyst 133 is positioned in a catalyst bed 1304 downstream of the inlet 131 and upstream of the outlet 134. The cavity 1320 has a length 1321 ranging from about 24 inches (60.96 centimeters) to about 1440 inches (3657.6 centimeters), a width 1322 ranging from about 1 inches (2.54 centimeters) to about 72 inches (182.88 centimeters), and a height 1323 ranging from about 48 inches (121.92 centimeters) to about 192 inches (487.68 centimeters). In various embodiments, the length 1321, width 1322, and height 1323 of the cavity is 1 in. (2.54 cm.); 2 in. (5.08 cm.); 3 in. (7.62 cm.); 4 in. (10.16 cm.); 5 in. (12.70 cm.); 6 in. (15.24 cm.); 7 in. (17.78 cm.); 8 in. (20.32 cm.); 9 in. (22.86 cm.); 10 in. (25.40 cm.); 20 in. (50.80 cm.); 25 in. (63.50 cm.); 30 in. (76.20 cm.); 40 in. (101.60 cm.); 50 in. (127.00 cm.); 60 in. (152.40 cm.); 70 in. (177.80 cm.); 72 in. (182.88 cm.); 75 in. (190.50 cm.); 80 in. (203.20 cm.); 90 in. (228.60 cm.); 100 in. (254.00 cm.); 100 in. (254.00 cm.); 110 in. (279.40 cm.); 120 in. (304.80 cm.); 130 in. (330.20 cm.); 140 in. (355.60 cm.); 150 in. (381.00 cm.); 160 in. (406.40 cm.); 170 in. (431.80 cm.); 180 in. (457.20 cm.); 190 in. (482.60 cm.); 192 in. (487.68 cm.); 200 in. (508.00 cm.); 300 in. (762.00 cm.); 400 in. (1016.00 cm.); 500 in. (1270.00 cm.); 600 in. (1524.00 cm.); 700 in. (1778.00 cm.); 800 in. (2032.00 cm.); 900 in. (2286.00 cm.); 1000 in. (2540.00 cm.); 1100 in. (2794.00 cm.); 1200 in. (3048.00 cm.); 1300 in. (3302.00 cm.); 1400 in. (3556.00 cm.); and 1440 in. (3657.60 cm.). In various embodiments, the length 1321, width 1322, and height 1323 of the cavity is between any two lengths, widths, and heights in this paragraph.

In one example, the converter is from the inlet sulfur dioxide, oxygen, and nitrogen connection through the converters to the effluent gas discharge. In this example system, the sulfur dioxide and oxygen are mixed, heated, passed through three stages of catalyst, optionally cooled and passed through a separator where the condensed sulfur trioxide collects. In the example, effluent gas from the sulfur trioxide receiver contains oxygen, sulfur dioxide, and sulfur trioxide. Before the effluent gas discharges to the effluent scrubber in the example, it is mixed with nitrogen to dilute the oxygen to a concentration of about 5% by volume.

Figure 4:
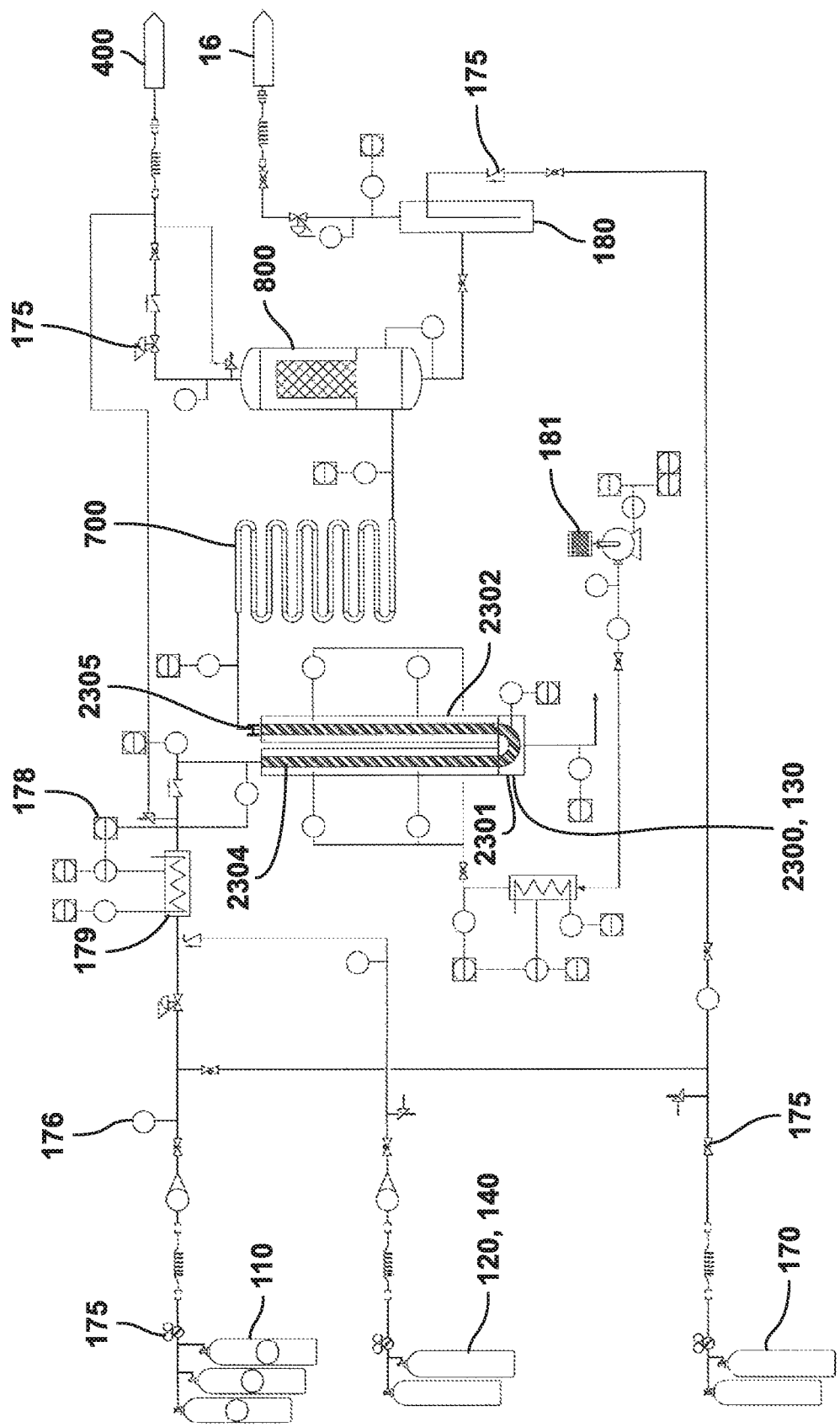

As shown in FIG. 4, the converter 130 is a sulfur dioxide to sulfur trioxide gas/liquid isothermic converter 2300 having at least two generally straight piping sections 2301 with a length 2303 and a pipe bend section 2302 arranged between the at least two generally straight piping sections 2301 and the piping sections each have a bore 2304 with a diameter 2305 defining the cavity 132 containing the catalyst 133. In various embodiments, the length 2303 and/or bore diameter 2305 is 1 in. (2.54 cm.); 2 in. (5.08 cm.); 3 in. (7.62 cm.); 4 in. (10.16 cm.); 5 in. (12.70 cm.); 6 in. (15.24 cm.); 7 in. (17.78 cm.); 8 in. (20.32 cm.); 9 in. (22.86 cm.); 10 in. (25.40 cm.); 20 in. (50.80 cm.); 24 in. (60.96 cm.); 30 in. (76.20 cm.); 40 in. (101.60 cm.); 50 in. (127.00 cm.); 60 in. (152.40 cm.); 70 in. (177.80 cm.); 72 in. (182.88 cm.); 80 in. (203.20 cm.); 90 in. (228.60 cm.); 100 in. (254.00 cm.); 150 in. (381.00 cm.); 200 in. (508.00 cm.); 250 in. (635.00 cm.); 300 in. (762.00 cm.); 350 in. (889.00 cm.); 400 in. (1016.00 cm.); 450 in. (1143.00 cm.); and 480 in. (1219.20 cm.). In various embodiments, the length 2303 and/or bore diameter 2305 is between any two lengths/diameters in this paragraph.

In various embodiments, sulfur trioxide generating system 100, 100", 100'" includes a heater 150 operable to heat sulfur or oxygen dispensed from the portable sources 110, 120, 140 to a temperature sufficient for generating sulfur trioxide. The heater 150 is thermally coupled 154 to piping as shown in FIGS. 1, 2A-2B, 5A-5B, and 6 to maintain the sulfur trioxide generating system 100, 100", 100'" at a temperature of at least 50° F. (10° C.) when sulfur trioxide is being generated and/or dispended. The heater 150 is also thermally coupled 155 to the converter 130 to heat sulfur or oxygen dispensed from the portable sources to a temperature of 500° F. (260.00° C.), 600° F. (315.56° C.), 700° F. (371.11° C.), 800° F. (426.67° C.), 900° F. (482.22° C.), 1000° F. (537.78° C.), 1100° F. (593.33° C.), 1200° F. (648.89° C.), 1300° F. (704.44° C.), 1400° F. (760.00° C.), 1500° F. (815.56° C.), 1600° F. (871.11° C.), 1700° F. (926.67° C.), 1800° F. (982.22° C.), 1900° F. (1037.78° C.), and 2000° F. (1093.33° C.). In various embodiments, the heater 130 can heat sulfur or oxygen dispensed from the portable sources 110, 120 to a temperature between two of any temperatures in this paragraph. The heater 150 can include, for example, various type electrical heaters, air heaters, heating blankets, and preheater. In various embodiments, the length 151, width 152, and height 153 of the heater 150 is 2 in. (5.08 cm.); 3 in. (7.62 cm.); 4 in. (10.16 cm.); 5 in. (12.70 cm.); 10 in. (25.40 cm.); 20 in. (50.80 cm.); 30 in. (76.20 cm.); 40 in. (101.60 cm.); 50 in. (127.00 cm.); 60 in. (152.40 cm.); 70 in. (177.80 cm.); 72 in. (182.88 cm.); 100 in. (254.00 cm.); 150 in. (381.00 cm.); 200 in. (508.00 cm.); 250 in. (635.00 cm.); 300 in. (762.00 cm.); 350 in. (889.00 cm.); 400 in. (1016.00 cm.); 450 in. (1143.00 cm.); and 480 in. (1219.20 cm.). In various embodiments, the length 151, width 152, and height 153 of the heater 150 is between any two lengths, widths, and heights in this paragraph.

The sulfur trioxide generating system 100, 100", 100'" of various embodiments includes a plurality of conduits 160 connecting the various components of the sulfur trioxide generating system 100, 100", 100'". The plurality of conduits 160 are preferably flexible. As shown in FIG. 3, the plurality of conduits 160 are preferably insulated and/or thermally coupled to the heater such that the temperature of fluids and gases flowing through the plurality of conduits 160 are kept at temperature of at least 50° F. (10° C.) when sulfur trioxide is being generated and/or dispended. For insulation, the plurality of conduits can be substantially covered with a jacket 165 made up of an insulative material, which preferably covers the plurality of conduits 160 that are exposed to outside elements. In various embodiments, the insulative jacket 165 covers all of the plurality of conduits 160 to maintain the temperature of fluids and gases flowing through the plurality of conduits 160 at least 50° F. (10° C.). In various embodiments, the sulfur trioxide generating system 100, 100", 100'" includes pipe heating cables 166 that are thermally coupled to the 150. As shown in FIG. 3, the heating cables 166 wrapped around the plurality of conduits such that the heating cables 166 are positioned on the outer surface of the plurality of conduits 160, which preferably covers the plurality of conduits 160 that are exposed to outside elements. In various embodiments, the heating cables 166 covers all of the plurality of conduits 160 to maintain the temperature of fluids and gases flowing through the plurality of conduits 160 at least 50° F. (10° C.). In alternative embodiments, the insulative jacket 165 and pipe heating cables 166 can be incorporated within the conduits to maintain the temperature of fluids and gases flowing through the plurality of conduits 160 at least 50° F. (10° C.). As shown in FIGS. 1A-1B and 2A-2C, the plurality of conduits includes conduit 161 connecting the sources of sulfur 110 and oxygen 120, 140 to the converter 130 and discharge conduit 162 directing sulfur trioxide from the converter 130 to the site 16.

As shown in FIGS. 1, 2A-2B, 5A-5B, and 7, the sulfur trioxide generating system 100″, 100‴ of various embodiments includes a portable source of a flushing/pressure maintaining liquid or gas 170 fluidly or gaseously coupled to the inlet of the converter 130. The portable source of a flushing/pressure maintaining liquid or gas 170 is capable of dispensing a gas or liquid to supplement the pressure in the sulfur trioxide generating system 100″, 100‴ or flushing sulfur trioxide in the sulfur trioxide generating system 100″, 100‴ after the sulfur trioxide has been dispensed to a site 16. The portable source of a flushing/pressure maintaining liquid or gas 170 can be a storage container storing an amount of 5 lbs. (2.27 kg.); 6 lbs. (15.24 kg.); 7 lbs. (17.78 kg.); 8 lbs. (20.32 kg.); 9 lbs. (22.86 kg.); 10 lbs. (25.40 kg.); 50 lbs. (127.00 kg.); 100 lbs. (254.00 kg.); 200 lbs. (508.00 kg.); 300 lbs. (762.00 kg.); 400 lbs. (1016.00 kg.); 500 lbs. (1270.00 kg.); 600 lbs. (1524.00 kg.); 700 lbs. (1778.00 kg.); 800 lbs. (2032.00 kg.); 900 lbs. (2286.00 kg.); and 1000 lbs. (2540.00 kg.). The portable source of the flushing/pressure maintaining liquid or gas 170 of various embodiments is pressurized liquid nitrogen. Also, the length 171, width 172, height 173 or diameter 174 of the portable source of the flushing/pressure maintaining liquid or gas 170 is 1 ft. (30.48 cm.); 2 ft. (60.96 cm.); 3 ft. (91.44 cm.); 4 ft. (121.92 cm.); 5 ft. (152.40 cm.); 6 ft. (182.88 cm.); 7 ft. (213.36 cm.); 8 ft. (243.84 cm.); 9 ft. (274.32 cm.); 10 ft. (304.80 cm.); 11 ft. (335.28 cm.); 12 ft. (365.76 cm.); 13 ft. (396.24 cm.); 14 ft. (426.72 cm.); 15 ft. (457.20 cm.); 16 ft. (487.68 cm.); 20 ft. (609.60 cm.); 25 ft. (762.00 cm.); 30 ft. (914.40 cm.); 35 ft. (1066.80 cm.); 40 ft. (1219.20 cm.); 45 ft. (1371.60 cm.); and 48 ft. (1463.04 cm.). In various embodiments, the length 171, width 172, height 173, or diameter 174 of the heater 150 of the portable source of the flushing/pressure maintaining liquid or gas 170 is between any two lengths, widths, heights, and diameters in this paragraph. The plurality of conduits 160 also includes a conduit 163 gaseously or fluidly connecting the portable source of the flushing/pressure maintaining liquid or gas 170 to either the converter 130, the discharge conduit 162, or both.

Figure 5A:
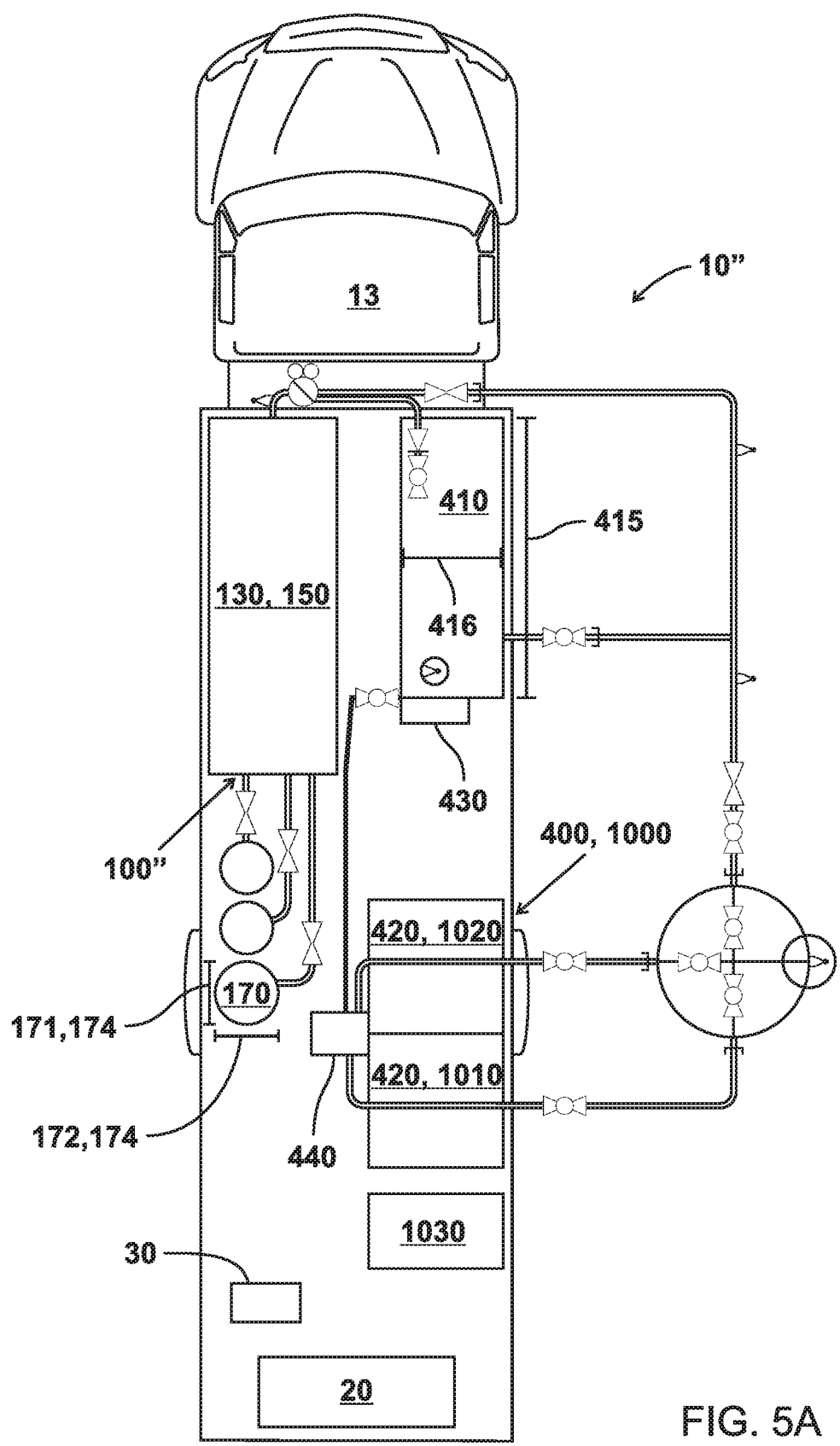
FIGS. 5A and 5B show an apparatus and system of various embodiments mounted on a transportable base and substantially enclosed by an enclosure, where the transportable base is capable of transport with a vehicle.
Figure 5B:
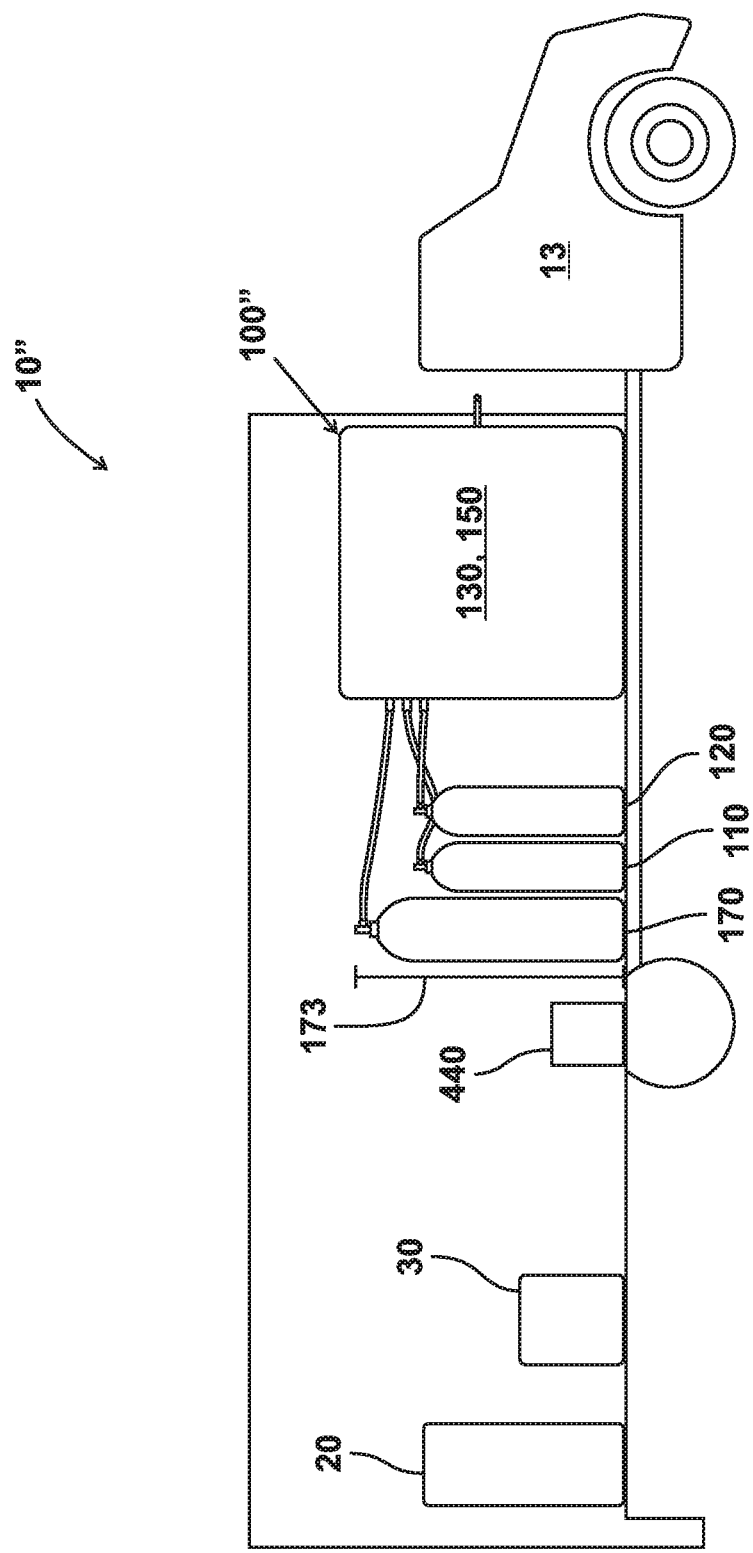
Figure 7:
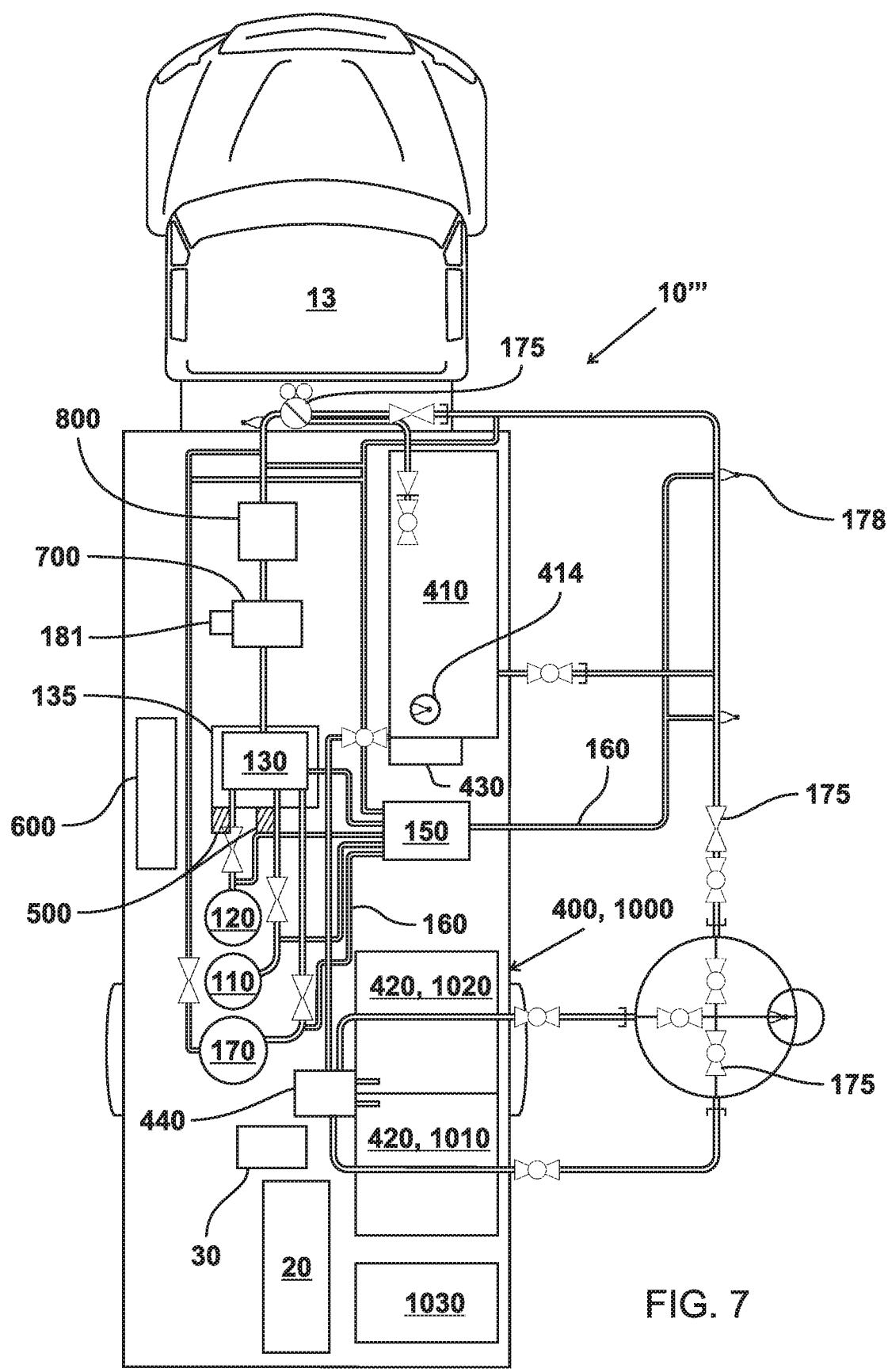
FIG. 7 shows an apparatus and system of various embodiments mounted on a transportable base and substantially enclosed by an enclosure, where the transportable base is capable of transport with a vehicle.

In one example, nitrogen is supplied from high pressure compressed gas cylinders. In the example, the nitrogen pressure is let-down in pressure using relieving regulator to supply nitrogen to the process. In the example, the node goes from the cylinders to the isolation solenoids As shown in FIGS. 5A-5B and 7, the sulfur trioxide generating system 100″, 100‴ of various embodiments includes a scrubbing system 400 supported by the transportable base and comprising a mist eliminator/scrubber 410 fluidly or gaseously coupled to the outlet 134 of the converter 130, a portable source of a neutralizing agent 420 fluidly or gaseously coupled to the mist eliminator/scrubber 410, and a pump 430 operable to recirculate the neutralizing agent between the mist eliminator/scrubber 410 and the source of the neutralizing agent 420. The scrubbing system 400 is operable to receive gases from the converter 130 and neutralize the gases. In various embodiments, the scrubbing system 400 can include a second pump 440, where both pumps 430,440 are operable to recirculate the neutralizing agent between the mist eliminator/scrubber 410 and the source of the neutralizing agent 420.

As shown in FIG. 6, the mist eliminator/scrubber 410 of various embodiments has an inlet 411 for receiving gases from the converter 130 or discharge conduit 162, a cavity containing a fiberbed membrane 412, a spray 413 operable to receive neutralizing agent from the portable source 420 and discharge/soak the fiberbed membrane 412 with the neutralizing agent, and a vent 414 gaseously communicating with the cavity of the mist eliminator/scrubber 410 and capable of venting to an outside environment. The length 415, width 416, or height 417 of the mist eliminator/scrubber 410 is 2 ft. (60.96 cm.); 3 ft. (91.44 cm.); 4 ft. (121.92 cm.); 5 ft. (152.40 cm.); 6 ft. (182.88 cm.); 7 ft. (213.36 cm.); 8 ft. (243.84 cm.); 9 ft. (274.32 cm.); 10 ft. (304.80 cm.); 11 ft. (335.28 cm.); 12 ft. (365.76 cm.); 13 ft. (396.24 cm.); 14 ft. (426.72 cm.); 15 ft. (457.20 cm.); 16 ft. (487.68 cm.); 17 ft. (518.16 cm.); 18 ft. (548.64 cm.); 19 ft. (579.12 cm.); 20 ft. (609.60 cm.); 21 ft. (640.08 cm.); 22 ft. (670.56 cm.); 23 ft. (701.04 cm.); and 24 ft. (731.52 cm.). In various embodiments, the length 415, width 416, and height 417 of the mist eliminator/scrubber 410 is between any two lengths, widths, and heights in this paragraph.

The portable source of a neutralizing agent 420 of various embodiments include caustic or positive ion agents include sodium hydroxide. The portable source of a neutralizing agent 420 of various embodiments is a storage container or bag storing an amount of neutralizing agent ranging from 5 lbs. (2.27 kg.); 10 lbs. (4.54 cm.); 50 lbs. (22.68 cm.); 100 lbs. (45.36 cm.); 500 lbs. (226.80 cm.); 1000 lbs. (453.59 cm.); 1500 lbs. (680.39 cm.); 2000 lbs. (907.18 cm.); 2500 lbs. (1133.98 cm.); 3000 lbs. (1360.78 cm.); 3500 lbs. (1587.57 cm.); 4000 lbs. (1814.37 cm.); 4500 lbs. (2041.17 cm.); and 5000 lbs. (2267.96 cm.). In various embodiments, the amount of neutralizing agent contained in portable source 420 is between any two amount in this paragraph.

The length 421, width, 422, height 433, or diameter of the portable source of a neutralizing agent 420 is 2 ft. (60.96 cm.); 3 ft. (91.44 cm.); 4 ft. (121.92 cm.); 5 ft. (152.40 cm.); 6 ft. (182.88 cm.); 7 ft. (213.36 cm.); 8 ft. (243.84 cm.); 9 ft. (274.32 cm.); 10 ft. (304.80 cm.); 11 ft. (335.28 cm.); 12 ft. (365.76 cm.); 13 ft. (396.24 cm.); 14 ft. (426.72 cm.); 15 ft. (457.20 cm.); 16 ft. (487.68 cm.); 17 ft. (518.16 cm.); 18 ft. (548.64 cm.); 19 ft. (579.12 cm.); 20 ft. (609.60 cm.); 21 ft. (640.08 cm.); 22 ft. (670.56 cm.); 23 ft. (701.04 cm.); 24 ft. (731.52 cm.); 25 ft. (762.00 cm.); 30 ft. (914.40 cm.); 35 ft. (1066.80 cm.); and 40 ft. (1219.20 cm.). In various embodiments, the length 421, width, 422, height 433, or diameter of the portable source of a neutralizing agent 420 is between any length, width, height, or diameter in the paragraph.

As shown in FIG. 7, the sulfur trioxide generating system 100‴ includes a humidity removal element 500 capable of removing humidity from the portable sources of sulfur and/or oxygen. The humidity removal element 500 of various embodiments includes a dessicant dryer. In various embodiments, the humidity removal element 500 preferably removes humidity from the air from the air compressor 140 or oxygen from the portable source 120 up to about −180° F. (−117.78° C.) dew point. In various embodiments, the humidity removal element 500 preferably removes humidity from the air from the air compressor 140 or oxygen from the portable source 120 to a dew point of at least about −85° F. (−65° C.). In various embodiments, the humidity removal element 500 preferably removes humidity from the air from the air compressor 140 or oxygen from the portable source

120 to a dew point of −80° F. (−62.22° C.); −90° F. (−67.78° C.); −100° F. (−73.33° C.); −110° F. (−78.89° C.); −120° F. (−84.44° C.); −130° F. (−90.00° C.); −140° F. (−95.56° C.); −150° F. (−101.11° C.); −160° F. (−106.67° C.); −170° F. (−112.22° C.); and −180° F. (−117.78° C.). In various embodiments, the dew point is between any two dew points in this paragraph.

As shown in FIGS. 1, 2A-2B, 3-4, 5A-5B, 6, and 7, the sulfur trioxide generating system 100, 100", 100''' includes a sensor or a plurality of sensors including, for example, various indicators 176, transmitters, recorders, controllers 178, elements 177, gauges, transducers, heat exchangers 180 and alarms that are coupled to various components of the sulfur trioxide generating system. The indicators of various embodiments include, for example, temperature indicators, flow indicators, pressure indicators, and level indicators operable to acquire information when the sulfur trioxide generating system or any system of the present is in operation. The transmitters of various embodiments include, for example, temperature transmitters, flow transmitters, pressure transmitters, analyzer transmitters, and level transmitters operable to transmit the information. The recorders of various embodiments include, for example, temperature recorders, flow recorders, pressure recorders, and level recorders operable to record the information. The controllers of various embodiments include, for example, temperature controllers, flow controllers, pressure controllers, level controllers, pressure indicating controllers, and pressure recording controllers operable to control operation of the sulfur trioxide generating system or any system of any embodiment. The elements of various embodiments, include, for example, flow elements and temperature elements operable to provide output that can got to a controller. The gauge of various embodiments, include, for example, temperature gauges, flow gauges, pressure gauges, and level gauges capable of display information when the sulfur trioxide generating system or any system of any embodiment is in operation. The alarms of various embodiments include, for example, temperature alarms, flow alarms, pressure alarms, and level alarms capable of alerting a user when the sulfur trioxide generating system or any system of any embodiment is not operating in a pre-determined manner.

As shown in FIGS. 1A-1B, 2A-2C, 3, 4A-4C, and 5A-5C, the sulfur trioxide generating system 100, 100", 100''' includes a valve or a plurality of valves 175 coupled to the various components of the sulfur trioxide generating system and operable to regulates, directs or control the flow of a fluid by opening, closing, or partially obstructing passageways. The valves 175 of various embodiments can include rotameters, orifices, and other types of valves.

As shown in FIGS. 5A-5C, the sulfur trioxide generating system 100''' can include: a main controller 600 coupled to receive information from the plurality of sensors, having a display for the received information, and operable to engage and control the plurality of controllers; a sulfur trioxide cooler 700 fluidly or gaseously coupled to the outlet and capable of cooling the sulfur trioxide to a liquid and separating oxygen from the generated sulfur trioxide; a mist eliminator/oleum separator 800 coupled to the sulfur trioxide cooler 700 and capable of separating oleum form the generated sulfur trioxide. The Control System 600 can be mounted on the converter 130 and can monitor the system 100, 100", 100''' and regulates the flow, temperatures and pressures of the different liquids and gases. The system 100, 100", 100''' is programmed to produce a specific volume of sulfur trioxide gas and/or liquid.

Also as shown in in FIGS. 5A-5C, the apparatus 10''' can include an electrical generator 20 supported by the transportable base 200''' and operable to provide electricity to the sulfur trioxide generating system 100''' as well as the apparatus 10''' and a space heater 30 supported by the transportable base 200''' and operable to maintain the sulfur trioxide generating system 100''' at a temperature of at least about 50° F. (10° C.).

As shown in FIGS. 5A-5C, apparatus, systems, and methods 10''' for removing hydrocarbon contaminants build-up on and treating surfaces including: a sulfur trioxide generating system 100'''; and a neutralizing system 1000 having a portable source of a neutralizing agent 417, a conduit 163 coupled to the portable source of the neutralizing agent 420, and a pump 440 operable to pump the neutralizing agent from the portable source and through the conduit; a transportable base adapted to support the sulfur trioxide generating and neutralizing systems and is transportable to a site when supporting the sulfur trioxide generating and neutralizing system; wherein the sulfur trioxide generating is operable to generate and dispense sulfur trioxide and neutralizing system is operable to dispense the neutralizing agent at the site. In various embodiments, the portable source of a neutralizing agent 417 includes portable sources of a caustic agent, positive ion neutralizing fluid/gas 1010, water 1020, or mixtures thereof. The caustic agent or positive ion neutralizing fluid/gas 1010 of various embodiments is sodium hydroxide or a solution of sodium hydroxide. The apparatus, systems, and methods 10''' can also include storage 1030 for solid/flaky or concentrated solutions of the caustic agent or positive ion neutralizing fluid/gas.

In various embodiments are disclosed methods for producing or extracting hydrocarbons including the steps of generating sulfur trioxide at or near a well-site of a deposit containing a clathrate hydrate such as methane hydrate, delivering the sulfur trioxide to the deposit where the sulfur trioxide reacts with the clathrate hydrate to generate a hydrocarbon gas, and recovering the hydrocarbon gas. The transportable apparatus 10, 10', 10", 10''' or sulfur trioxide generating system 100, 100", 100''' of any embodiment can be used for generating sulfur trioxide used in the method of producing hydrocarbons of various embodiments.

The sulfur trioxide of various embodiments is prepared by combining a stream of sulfur with a stream of oxygen or air containing oxygen and catalyzing a reaction of the sulfur and oxygen in the combined stream and/or is generated at a rate of about 0.5 gallons (1.89 liters) per hour to about 2000 gallons (7570.82 liters) per hour. The hydrocarbon gas of various embodiments is at least one of methane, ethane, butane, propane, or mixtures thereof.

In various embodiments, the generated sulfur trioxide is combined a medium including, for example, nitrogen or air that is delivered to the deposit. The medium of various embodiments can be a gas or liquid. The medium of various embodiments can also be pressurized for delivery to the deposit. When delivered to the deposit, the sulfur trioxide can exothermically react with water as shown below.

$$SO_3 + H_2O \rightarrow H_2SO_4 \Delta H < 0$$

The heat generated in the reaction of 1 mole of sulfur trioxide and 1 mole of water can be −176,000 kj/kmol. The sulfur trioxide can also exothermically react with hydrocarbons such as aromatic hydrocarbons as shown below.

$$RH + SO_3 \rightarrow RSO_3H \Delta H < 0$$

In this example R is a hydrocarbon and RSO₃H is a sulfonic acid. The heat generated in the reaction of 1 mole of sulfur trioxide and 1 mole of an aromatic hydrocarbon can be −155,000 kj/kmol. In both reactions, the generated heat can melt paraffin deposits.

The method of various embodiments can also include the step of flushing the generated sulfur trioxide from the transportable apparatus, sulfur trioxide generating system, casing, or tubular.

The sulfur trioxide of various embodiments can also react with the clathrate hydrate or water to produce sulfuric acid, heat, and sulfonated derivatives such as alkylsulfonic acids, alkyl alcohols, or alkyl esters of the sulfonic acids. In other embodiments, generated sulfuric acid can also react with the clathrate hydrate to generate reactions products.

Examples of sulfonated derivatives includes a compound of formula (I),

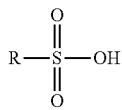

(I)

wherein R is linear or branched alkyl group with 1, 2, 3, 4 carbon atoms, or combinations thereof and the method further comprises the step of recovering the compound of formula (I) such as, for example, methane and sulfonic acid (CH₆O₄S). The compound of formula (I) includes isomers, enantiomers, or mixtures of different isomers or enantiomers.

Examples of the compound of formula (I) include:
a compound of formula (II),

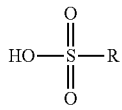

(II)

a compound of formula (III),

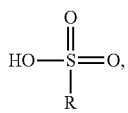

(III)

or
a compound of formula (IV),

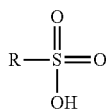

(IV)

wherein R is linear or branched alkyl group with 1, 2, 3, 4 carbon atoms, or combinations thereof and the method further comprises the step of recovering the compound of formula (I) such as, for example, methane and sulfonic acid (CH₆O₄S). The compound of formula (I) includes isomers, enantiomers, or mixtures of different isomers or enantiomers.

In one example, the compound of formula (I) is methanesulfonic acid or a compound of formula (V),

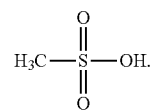

(V)

In one example, the compound of formula (I) is ethanesulfonic acid or a compound of formula (VI),

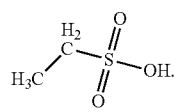

(VI)

In one example, the compound of formula (I) is propane-1-sulfonic acid or a compound of formula (VII),

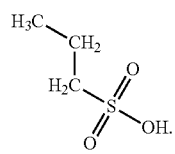

(VII)

In one example, the compound of formula (I) is propane-2-sulfonic acid or a compound of formula (VIII),

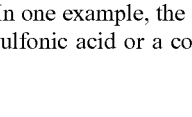

(VIII)

In one example, the compound of formula (I) is butane-1-sulfonic acid or a compound of formula (IX),

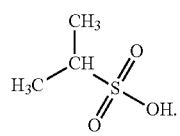

(IX)

In one example, the compound of formula (I) is butane-2-sulfonic acid or a compound of formula (X),

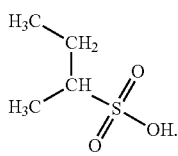

(X)

In various embodiments, sulfur trioxide reacts with the clathrate hydrate to produce sulfonated derivatives include any one of compounds of formula (I), (II), (III), (IV), (V), (VI), (VII), (VIII), (IX), or (X) or mixtures of any one of compounds of formula (I), (II), (III), (IV), (V), (VI), (VII), (VIII), (IX), or (X).

In various embodiments, the methods further includes providing a transportable system for on-demand sulfur trioxide generation at or near a well-site of a deposit containing a clathrate hydrate, the transportable system having a portable source of sulfur, a portable source of oxygen or air containing oxygen, and a converter fluidly or gaseously coupled to the portable source of sulfur and the portable source of oxygen or air and capable of catalyzing a reaction to generate sulfur trioxide from the sulfur and oxygen, wherein sulfur and oxygen are dispensed from the portable sources to generate sulfur trioxide and the transportable system has dimensions allowing for transport to or near the well-site.

In various embodiments, the methods further include the step of extracting the linear or branched alkyl group from the compound of formula (I) and/or capturing the compound of formula (I).

Figure 11:
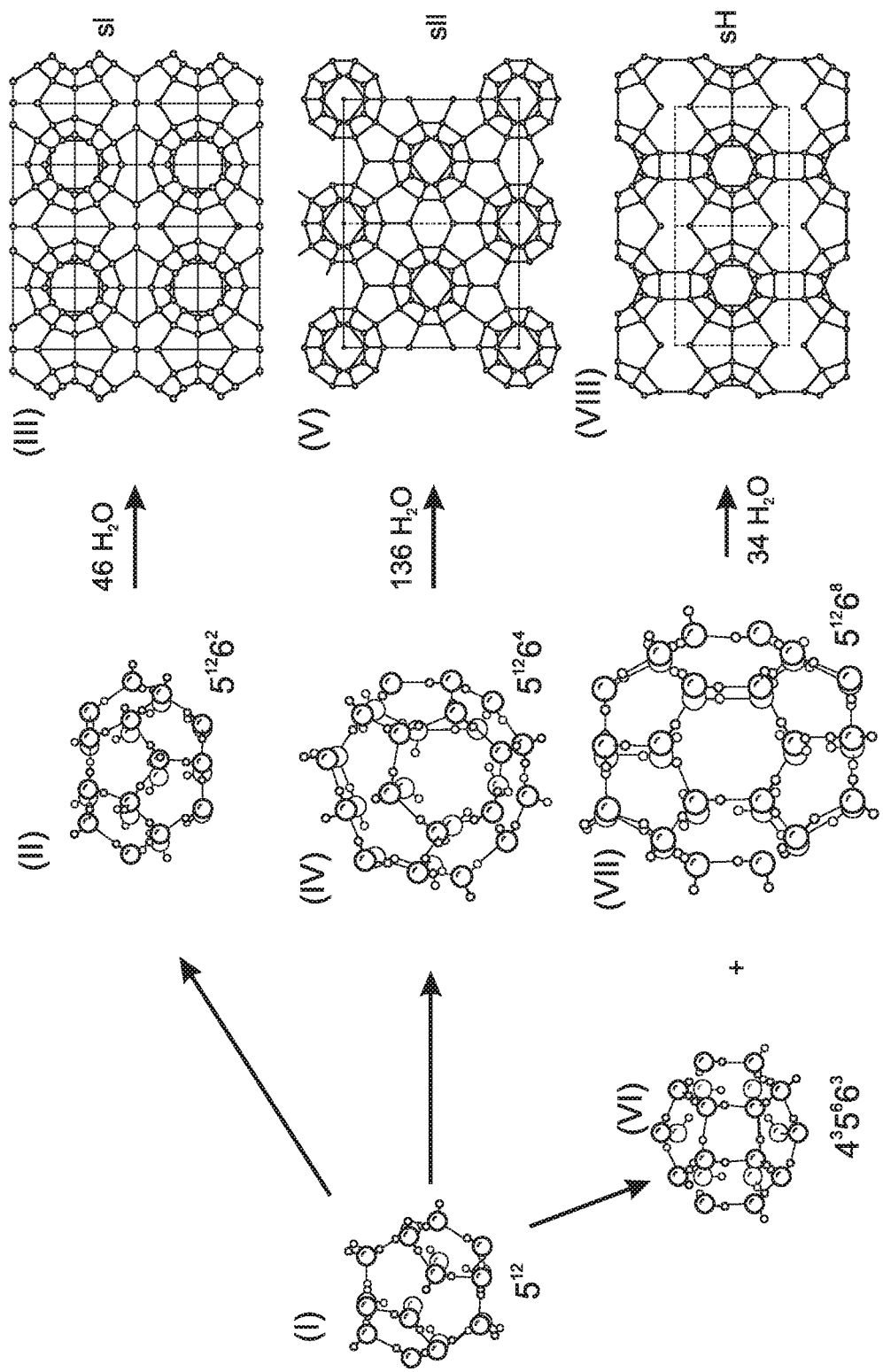
FIG. 11 shows different hydrate structures of clathrate hydrate.
Figure 12:
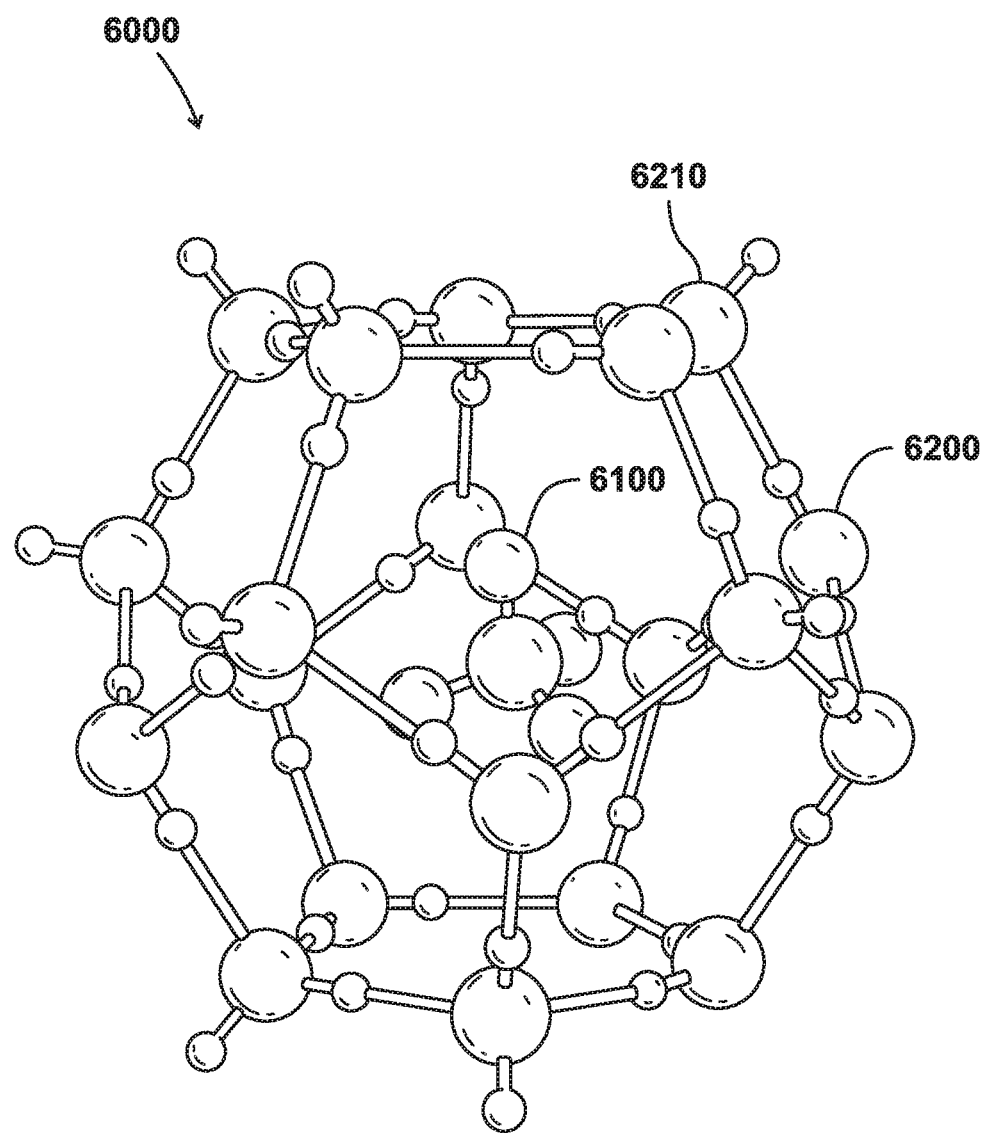
FIG. 12 shows the structure of a methane clathrate hydrate.

As disclosed in Hester, Keith C., and Peter G. Brewer. "Clathrate hydrates in nature." Annual review of marine science 1 (2009): 303-327, which is incorporated in its entirety by reference, clathrate hydrates are crystalline compounds formed from water cages stabilized by guest molecules through van derWaals-type interactions. Clathrate hydrates are generally classified on the basis of crystal structure. FIG. 11 shows different hydrate structures of clathrate hydrate. Each structure contains the small, nearly spherical $5^{12}$ cage (I of FIG. 11) combined with larger cages in various ratios to form a repeating unit cell. The water cages are described using the notation XY, where X is the number of sides per cage face and Y is the number of those face types that make up a particular cage. The relationship between the guest molecule, the cage sizes, and their ratios in the lattice largely determine which structure will form, especially for simple (single guest) hydrate systems. As shown in I, II, and III of FIG. 11, structure I (sI) hydrate contains large $5^{12}6^2$ and small $5^{12}$ cages in a ratio of 3:1. Methane, carbon dioxide, and ethane crystallize in the sI lattice. As shown in I, IV, and V of FIG. 11, structure II (sII) contains the larger $5^{12}6^4$ cages, as well as $5^{12}$ cages, in a ratio of 1:2. Molecules too large to fit in the $5^{12}6^2$ cage, such as propane and isobutane, are examples of sII guests. As shown in I, VI, VII, and VIII of FIG. 11, Structure H (sH) contains three cage types: large $5^{12}6^8$, medium $4^35^63^3$, and small $5^{12}$ cages in a ratio of 1:2:3. Two guests are required to form sH, where one guest stabilizes the small and medium cages, such as methane, and a larger guest stabilizes the $5^{12}6^8$ cages, such as methylcyclohexane. All three structures have been identified in nature, including multiple structures coexisting in the same area. One example of a clathrate hydrate is methane clathrate hydrate 6000. FIG. 12 shows the structure of methane clathrate hydrate 6000 including methane 6100 within a spherical $5^{12}$ cage 6200 made up of water 62100.

Figure 8:
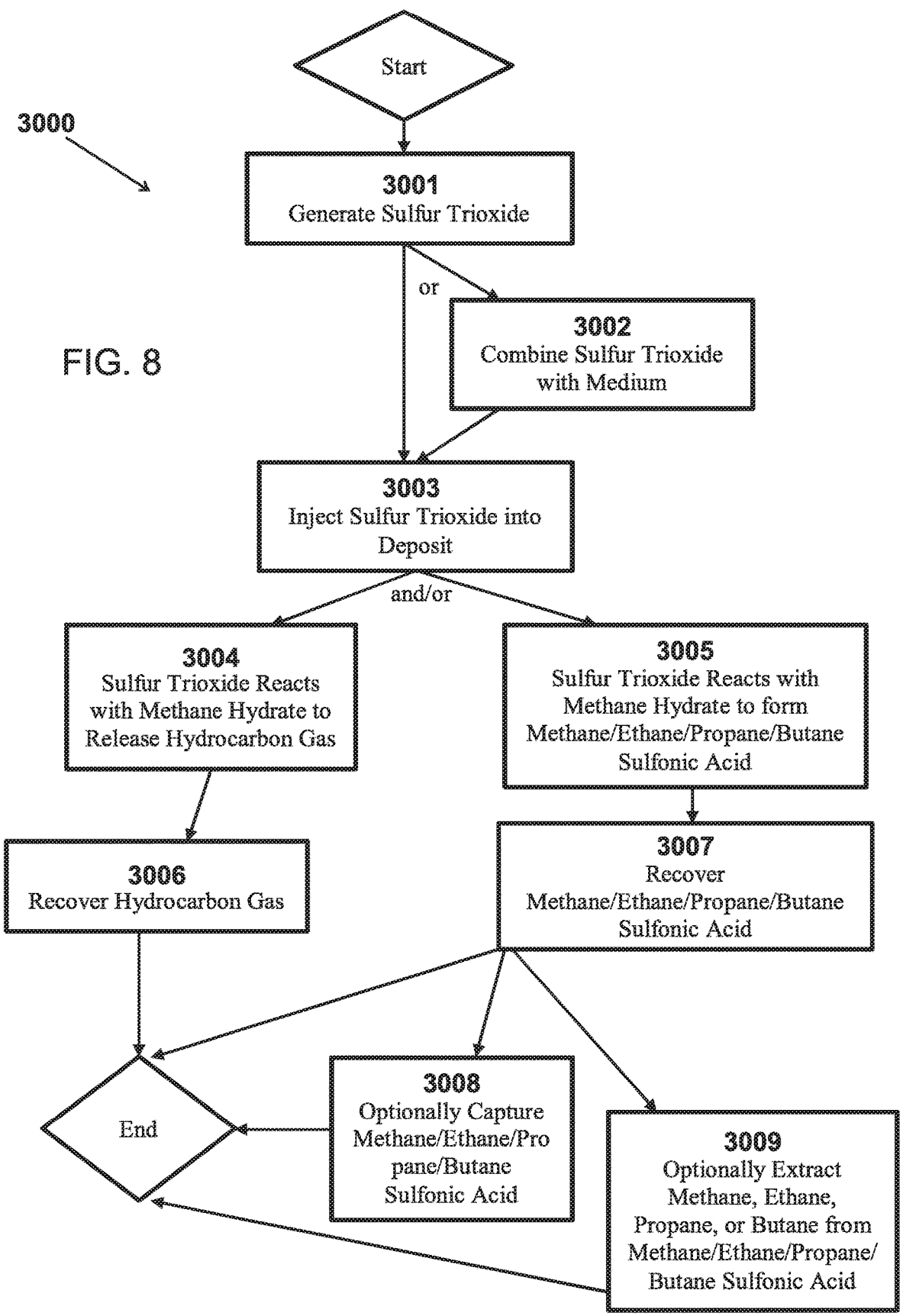
FIGS. 8 and 9 are flow charts outlining methods of producing hydrocarbons of various embodiments.
Figure 10:
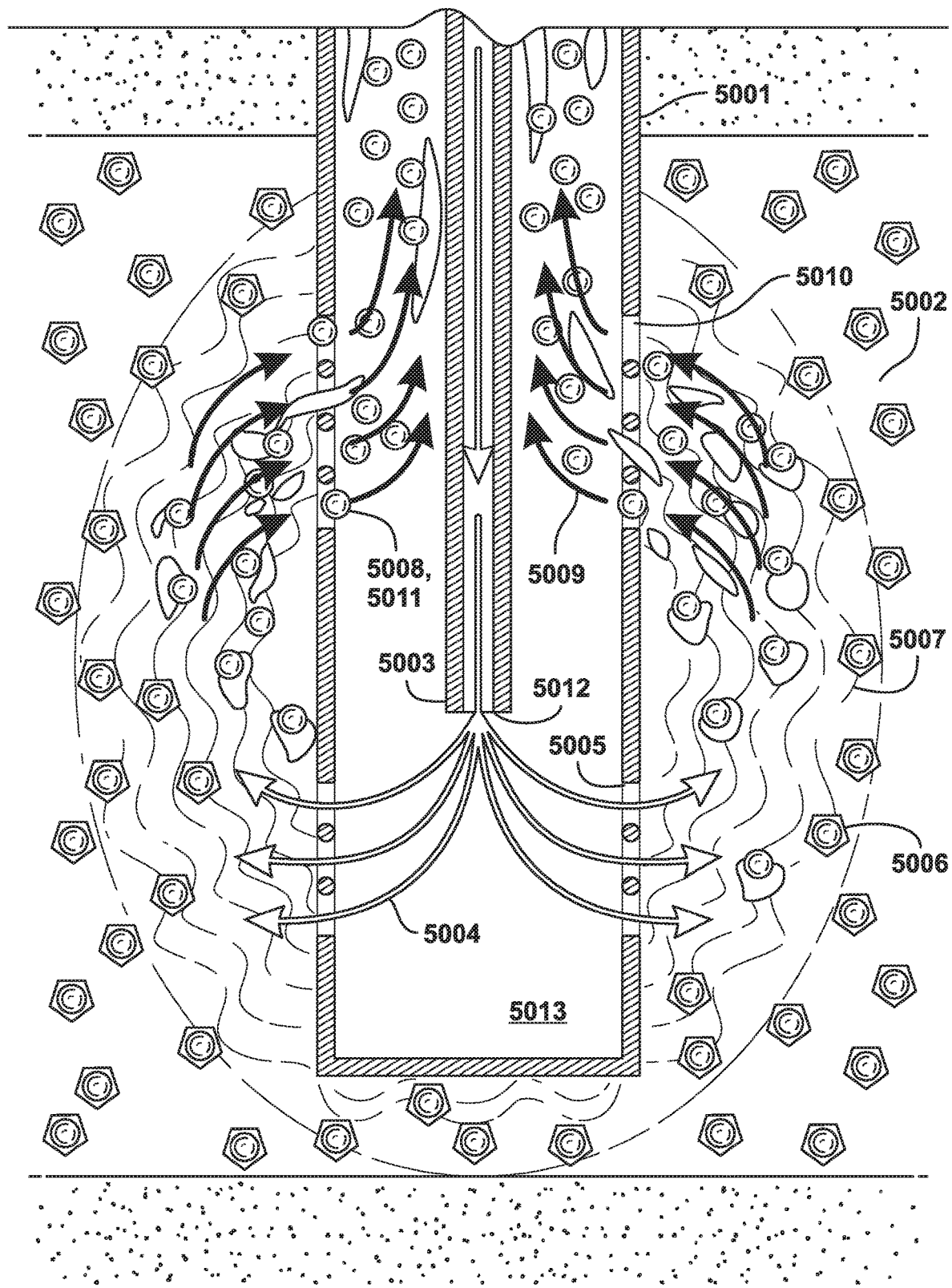
FIG. 10 shows methods of producing hydrocarbons of various embodiments.

As shown in FIG. 8 outlining the method 3000 of various embodiments and FIG. 10, the transportable apparatus 10,10',10",10'" or sulfur trioxide generating system 100, 100", 100'" of any embodiment generates sulfur trioxide 3001 at or near a well site for a deposit 5002 containing a methane hydrate 5006 or a clathrate hydrate (as shown in FIG. 10). The determination of whether a well site contains methane hydrates can include various processes such as inferences or other techniques such as field testing or seismic reflection techniques.

In step 3002, the sulfur trioxide generated in step 3001 and can be combined with a medium 3002 that can include, for example nitrogen and/or air. The medium of various embodiments can be a gas or liquid.

In step 3003, the sulfur trioxide is injected into the deposit 5002 where the sulfur trioxide reacts with the methane hydrates 5006 to release 3004 a hydrocarbon gas 5008 or forms 3005 a hydrocarbon sulfonic acid 5011 including, for example, methane sulfonic acid, ethane sulfonic acid, propane sulfonic acid, butane sulfonic acid, or combinations thereof. The hydrocarbon gas of various embodiments includes methane, ethane, butane, or combinations thereof.

In steps 3006 and 3007, the hydrocarbon gas 5008 and/or hydrocarbon sulfonic acid 5011 is recovered. Optionally, hydrocarbon sulfonic acid 5011 can be captured 3008 or treated to extract hydrocarbons 3009. In various embodiments, a system at least similar to the mist eliminator/scrubber 410 of various embodiments can be used to capture the hydrocarbon sulfonic acid 5011 or extract hydrocarbons from the hydrocarbon sulfonic acid 5011.

In various embodiments are disclosed methods of extracting hydrocarbons comprising the steps of delivering sulfur trioxide, as a liquid or gas, to a deposit containing a clathrate hydrate, where at least the sulfur trioxide reacts with the clathrate hydrate to produce a compound of formula (I),

(I)

wherein R is linear or branched alkyl group with 1, 2, 3, 4 carbon atoms, or combinations thereof; and recovering the compound of formula (I).

Figure 9:
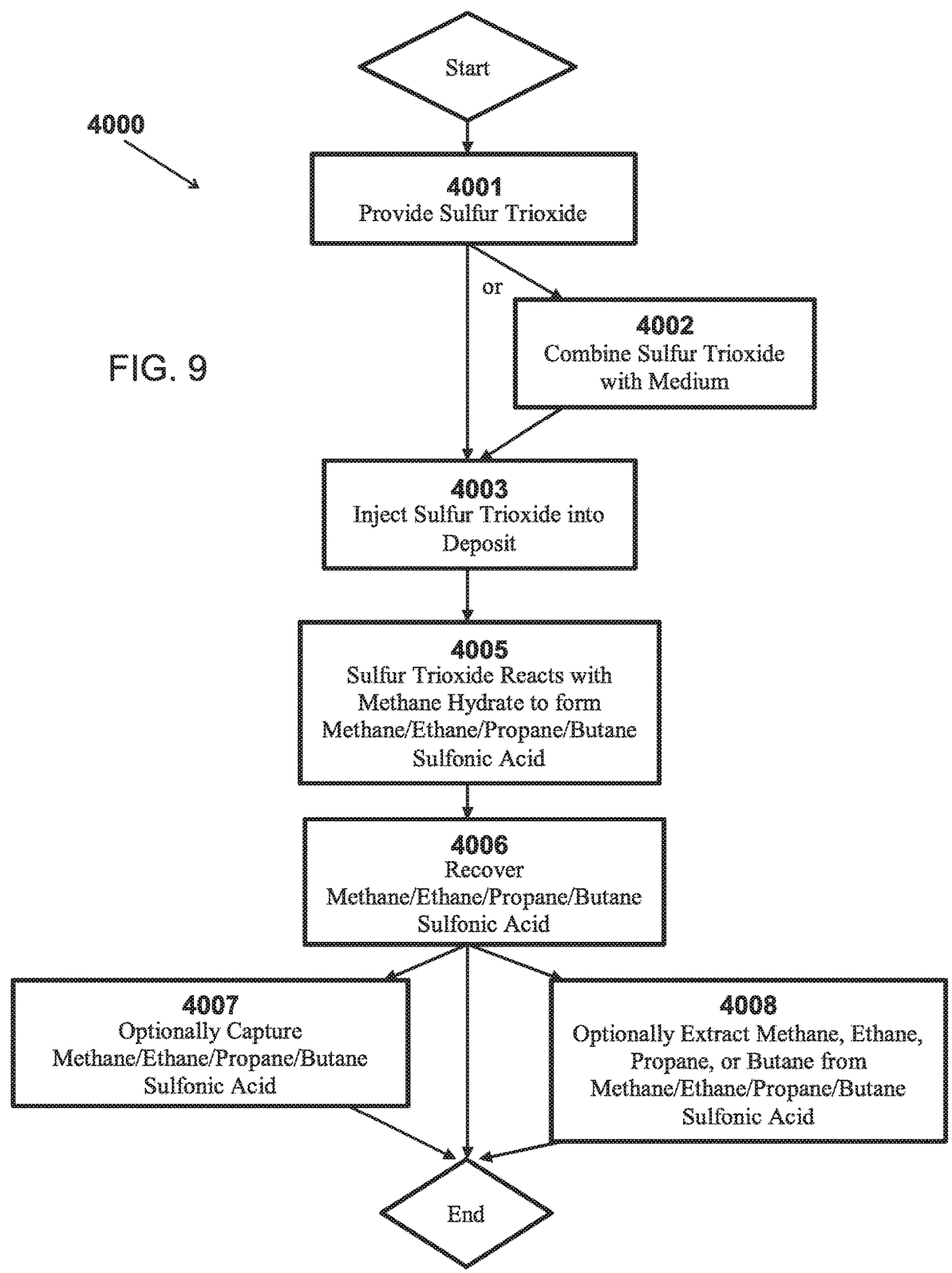

FIG. 9 outlines an alternative method 4000 of various embodiments, where sulfur trioxide is provided 4001. The sulfur trioxide can optionally be combined with a medium 4002 of various embodiments. The sulfur trioxide is injected 4003 into the deposit 5002, where the sulfur trioxide reacts 4002 with a methane hydrate 4005 or a clathrate hydrate to for a hydrocarbon sulfonic acid 5011. The hydrocarbon sulfonic acid 5011 is recovered 4006 and can be optionally captured 4007 or treated to extract 4008 hydrocarbons.

FIG. 10 is a diagram outlining the methods of extracting hydrocarbons 5008, 5011 from deposits 5002 containing a methane hydrate 5006 or a clathrate hydrate of various embodiments. Prior to flowing the sulfur trioxide, a casing 5001 is inserted into or formed within a deposit 5002. A tubular 5003 with a bore 5013 is inserted within to casing 5001 to a position near the deposit 5002. Sulfur trioxide is injected through the tubular 5003 and exits 5004 from the outlet 5005 in the wall of the casing 5001 to the bore 5013. The sulfur trioxide then exits 5004 from the outlet 5005 of the casing 5001 into the deposit 5002. The sulfur trioxide reacts the methane hydrates, where the reaction increase the temperature 5007 of the deposit. Thus, hydrocarbons 5008 and hydrocarbon sulfonic acids 5011 are produced. The reaction also produces sulfuric acids. The hydrocarbons 5008 and hydrocarbon sulfonic acids 5011 flow 5009 from the deposit 5002 and into the bore 5013 of the casing 5001 through inlets 5010 in the wall of the casing 5001. The hydrocarbons 5008 and hydrocarbon sulfonic acids 5011 are covered and can be processed for further applications.

In various embodiments, the delivering step includes maintaining the sulfur trioxide substantially always at a temperature of at least 50° F. (10° C.) or at a temperature where the sulfur trioxide does not crystalize. The tubular 5003 of various embodiments can be similar to the plurality of conduits 160 in being thermally connected to a heater such that the sulfur trioxide preferably is substantially always at a temperature of at least 50° F. (10° C.) or at a temperature where the sulfur trioxide does not crystalize. The tubular 5003 of various embodiments can include heating cables 166 positioned on the outer surface of the tubular 5003, where the heating cables are thermally coupled to a heating element. The tubular 5003 of various embodiments can also include a thermally insulated jacket 165 covering the outer surface of the tubular 5003.

The following examples illustrate the various embodiments of the present disclosure. Those skilled in the art will recognize many variations that are within the spirit of the present disclosure and scope of the claims.

In various examples are disclosed an improved method for treating crude oil and natural gas equipment surfaces to remove, inhibit and retard paraffins on equipment surfaces. The equipment surfaces include such equipment as pipelines both metal and polymeric, pumping equipment, valving, metering, transport lines, storage vessels and transport units. The new mobile unit/apparatus/system of any embodiment would preferably be transported to the wellsite or treatment location on a flatbed, cargo hauler or a cargo truck. The mobile unit/apparatus/system of any embodiment may also be shipped to the wellsite in a shipping container to a remote well location or an offshore well platform.

The mobile unit/apparatus/system of any embodiment is preferably capable of making sulfur trioxide liquid and/or gas on demand at the treatment location, the wellsite or location to treat tubing, transport lines, storage tanks and containers, pipe and additional equipment. This mobile unit/apparatus/system of any embodiment preferably eliminates the need to transport sulfur trioxide on the roadways or other means of transportation.

The control system/main controller of any embodiment is preferably mounted on the sulfur trioxide converter. The control system/main controller preferably monitors the whole system and regulates the flow, temperatures and pressures of the different liquids and gases. The control system/main controller of any embodiment is preferably programmed to produce a specific volume of sulfur trioxide gas and/or liquid.

The mobile unit preferably includes a number of process operations. Liquid sulfur dioxide preferably flows from the dip tube type storage cylinder and is preferably vaporized and regulated to the correct flow rate and pressure. The vaporized sulfur is preferably introduced into the converter.

Liquid oxygen is preferably stored in a container such as dewar cylinder and is vaporized and regulated to the correct flow and pressure. The vaporized oxygen is preferably introduced to the converter at a correct volume and pressure. Dry air may be substituted for the oxygen but results in a non-oxygen free sulfur trioxide.

The converter preferably combines the vaporized sulfur dioxide and oxygen and heats both gas to a temperature above 500° F. (260° C.) and up to 2000° F. (1093.33° C.). The gases preferably pass by a catalyst and are converted to sulfur trioxide. The sulfur trioxide with excess oxygen is preferably converted back to a liquid state and vaporized to remove the excess oxygen.

Liquid nitrogen is preferably supplied by a container such as a dewar cylinder and vaporized and heated. The nitrogen is preferably regulated to accurately measure the flow rate and pressure. The nitrogen gas is optionally supplements the sulfur trioxide to create the correct volume of sulfur trioxide gas stream going to the wellhead or item to be treated. The nitrogen gas can also be used to purge the converter of sulfur trioxide gas or liquid upon shutdown. The purged gas or liquid is preferably sent to the Mist Eliminator/Scrubber for neutralization. In other embodiments, dry air preferably at a minimum −85° F. (−65° C.) dew point is used in place of nitrogen gas The Mist Eliminator/Scrubber preferably receives purge gases and neutralizes the gases. The neutralization preferably occurs by the gases passing thru a fiberbed membrane that is sprayed with sodium hydroxide and water. The gases are preferably neutralized to a pH 7 and above. The neutralized gases are preferably converted to a liquid and are pumped back to the Sodium Hydroxide tank.

Once the converter is producing sulfur trioxide the fittings are preferably attached to the wellhead or parts by proper fittings for first the sulfur trioxide and, optionally nitrogen gases. Fitting are also preferably attached to the wellhead or parts for a sodium hydroxide and water flush.

The liquid or gas sulfur trioxide and, optionally, nitrogen or dry air are preferably moved under pressure to the wellhead or to the parts thru heated lines to prevent any crystallization of the sulfur trioxide. The control system/main controller of any embodiment preferably monitors the flow, temperature and pressure of the sulfur trioxide and nitrogen for the correct time to ensure proper treatment of the well and parts.

After the sulfur trioxide and nitrogen gas treatment has been completed, the converter is preferably turned off and nitrogen gas or dry air is preferably purged thru the converter. The purge is preferably sent to the Mist Eliminator/Scrubber where it is neutralized.

Upon completion of the sulfur trioxide and nitrogen gas to the wellhead or parts, the sodium hydroxide or other positive ion are preferably pumped to the wellhead or parts at up to 2000 gallons (7570.82 liters) per minute. The sodium hydroxide is preferably shut off and water is preferably pumped to the wellhead or parts at up to 2000 gallons (7570.82 liters) per minute.

After the water flush treatment is completed, the fitting/discharge conduits are preferably removed from the wellhead and the fitting and lines are preferably returned to the mobile unit. Once the purge is completed, the mobile unit is preferably available to treat a new well.

When necessary a heater may be needed in the mobile unit to maintain a temperature of a minimum of 70° F. (21.11° C.) preferably at all times.

The electricity is preferable to operate the system may be from an external source or can be provided by an Electric Generator.

In case of an emergency the operator can manually or remotely shut-off the power to the system and all valving will close except one which will discharge and gas still in the system to the Mist Eliminator/Scrubber.

The following are additional examples of various embodiments of the present disclosure.

A mobile apparatus unit, which is transported to the well location or area for treatment. The mobile unit would be an equipment trailer, such as a flatbed type trailer or shipping container or car trailer which would contain the apparatus and process for treating the surface that comes in contact with the paraffins, the paraffin surface or surfaces. For the purpose of this disclosure, "paraffins" means those molecules in the crude oil or natural gas such as hydrocarbons, waxes, asphaltenes and resins. The surfaces to be treated would be any equipment, valvings, pumps, transport lines, storage containers or vessels, gas wells or crude oil wells pipelines or other surfaces that are in contact with the crude oil or natural gas. The surfaces may be treated prior to installation while waiting to be installed such as storage locations or at the well sites on trailers, skids or in rolls.

The mobile unit would contain a generator, a source of oxygen and or air such as compressed air in tanks or air from an air compressor and receiver tank, air/gas dryer, raw sulfur with burner or sulfur dioxide in cylinders or tanks, an optional sulfur dioxide vaporizer, a nitrogen gas source such as a cylinder or dewar tank or a nitrogen gas generator or nitrogen membrane technology, a gas generator or several gas generators in parallel for sulfur dioxide to sulfur trioxide conversion via a vanadium catalyst or other catalyst or an isothermic converter or converters in parallel, with an optional oxygen removal system, optional mist eliminator or scrubber, heaters and controls to monitor flow rates, temperatures and moisture levels, tanks for water and a neutralizing agent such as sodium hydroxide or ammonia or other positive ion solutions, an optional Advanced Modification Systems Control Monitor which monitors such variables as temperature, air flow, oxygen flow, sulfur dioxide gas flow, nitrogen gas flow, and dew point level.

The generator would provide electricity for the processing equipment such as the air compressor, dryers, vaporizers, gas generator, heaters, pumps and controls.

The air compressor oil free or with oil filter will pump air to the air dryer or air dryers. The dry air or oxygen up to −180° F. (−117.78° C.) dew point, will flow to the gas generator/isothermic converter.

The sulfur dioxide from a source of raw sulfur or sulfur dioxide liquid or as a gas or a combination of these, will flow to the gas generator/isothermic converter.

The dry air or oxygen and sulfur dioxide gas, from up to 200 pounds (90.72 kilograms) of sulfur dioxide per hour, will pass the vanadium or other catalyst at a high temperature, up to 2000° F. (1093.33° C.), creating an oxygen free sulfur trioxide gas. Flow controls will determine the volume of sulfur trioxide liquid or gas generated.

The sulfur trioxide liquid and or gas optionally added to a gas stream of nitrogen gas or dry air or a combination of dry air and nitrogen or other inert gases to a controlled percentage of sulfur trioxide by volume, 2% to 100%.

The sulfur trioxide liquid and or gas in either dry air and/or nitrogen will flow at a flow rate controlled by flow meters and other controllers.

The sulfur trioxide liquid and or gas will be pushed by the pressure of the dry air or oxygen and sulfur and/or the pressure of the nitrogen gas thru heated lines to the surface to be treated, a vacuum pump may be optional to help the flow of gas thru pipe before installation. The sulfur trioxide liquid or gas when exposed to moisture at the area to be treated will create a thermal reaction up to 500° F. (260° C.). This thermal reaction will remove part or all of the paraffin buildup. The sulfur trioxide liquid or gas will also react with the paraffin and chemically modify the hydrocarbons.

After exposure to the sulfur trioxide liquid and or gas, an optional neutralization of a positive ion solution such as ammonia or sodium hydroxide, or a combination of alkaline solutions, diluted in water or water may be exposed to the surface neutralizing the sulfur trioxide and creating a hydrophilic, water-wettable surface.

The sulfur trioxide liquid and or gas and neutralizing solution or ammonia gas may be exposed to polymer pipeline such high-density polyethylene or nylon to remove the paraffins as well as exposing the interior of the pipeline rendering the polymer surface as a barrier for different solution. The polymer surface preferably becomes polar and provides a barrier for liquids and gases, such as hydrocarbons. The surface of the polymer may also be functionalized and/or metalized.

The sulfur trioxide liquid and or gas and neutralizing solution or ammonia gas may be exposed to metal pipe for oil and gas well applications and transport pipeline application also including metal surfaces on equipment used in the oil and gas industry. The treatment provides a water-wetting surface to inhibit future paraffin collection. This treatment can be done on new and used metal pipe and equipment.

The controls would be implemented to monitor the process for manual operation and/or computer control and/or electronic data interchange if desired.

The following are additional examples of various embodiments of the present disclosure.

The resulting sulfur dioxide and air mixture flows through a three-stage catalytic converter, which converts over 97% of the sulfur dioxide to sulfur trioxide. The converter vessel contains three beds of vanadium pentoxide catalyst for high conversion efficiencies. As the sulfur dioxide is oxidized to sulfur trioxide, heat is liberated which increases the gas temperature. Since the conversion of sulfur dioxide to sulfur trioxide is limited by temperature, the gas mixture is cooled by use of injection air between the first and second catalyst beds.

The sulfur trioxide gas leaves the converter at 440° C. (825° F.) and is first cooled in a double pipe sulfur dioxide cooler prior to final cooling to 43° C. (110° F.) by a water-cooled heat exchanger mounted on the gas generator skid. Traces of acid mist are separated from the cooled air mixture via an inlet mist eliminator vessel.

By liquefying the sulfur trioxide, the excess oxygen will be vented through your existing caustic effluent scrubber, rather than leaving with the sulfur trioxide. The liquid sulfur trioxide will then be vaporized and diluted with hot nitrogen before being sent out to the oil well. Some sulfur dioxide will be present in the vaporized product due to operating in reduced oxygen conditions.

Sulfur dioxide to sulfur trioxide Gas Generator System Designed to Produce up to 8 lb/hr (3.63 kg/hr) of sulfur trioxide Gas at a Pressure of −2.0 PSIG (13.79 kpa) and a Concentration of 12% (volume basis). System Includes: Liquid S02 Feed System (Rotameter & Valves); 02 Feed System (Rotameter & Valves); N2 Feed System (Rotameter & Valves); Liquid SO3 Separator/MistFilter; S02 to SO3 Isothermal Converter System with Cooling Jacket, Blower, Preheater, & Economizer; Liquid S03 Condenser; Liquid SO3 Separator/Mist Filter; Liquid SO3 Vaporizer; and Support Stand, Complete with Control Station.

Estimated Startup Time: 1-2 hours depending on experience & ambient conditions.

SO$_2$ Usage: 8 lb/hr (3.63 kg/hr) at 45 psi (31.02 kpa).

Air Usage: 30 SCFM (0.85 cubic meter per minute) at 6 psi (41.37 kpa) (Converter Cooling).

N$_2$ Usage: 19.4 lb/hr (8.8 kg/hr) at 30 psi (206.84 kpa)

Final SO$_3$ Flow: 8.0 lb/hr (3.63 kg/hr) at 2-30 psi (13.79 kpa-206.84 kpa)

Final SO$_3$ Volume: 5.1 SCFM (0.14 cubic meter per minute)

Electrical: 20 kW, 240V

Sulfur trioxide generating System Dimensions: 7'×7'×15' (213.36 cm×213.36×457.2 cm)

The scrubber is preferably rated for a nominal flow rate of 10 CFM (0.28 cubic meter per minute) at 100 psi (689.48 kpa) to remove sulfur trioxide fumes from the gas stream.

The Packed Tower Scrubbing System

Design Capacity: Up to 10 ACFM (0.28 cubic meter per minute) at 100 psi (689.48 kpa)

Approximate Dimensions: 2'-6" W (76.2 cm)×6'-0" L (182.88 cm)×7-2" H (218.44 cm)

Fresh Water Feed Rate: 6 GPM (22.71 liters per minute) Minimum

Recirculation Pump Motor: Up to 1½ HP, 3500 RPM, TEFC, 3/60/230/460

1st Stage Scrubber Vessel Construction: 304 SS

Scrubber Packing: 3 (7.62 cm)-6" (15.24 cm) of Loose Fill Media

2nd Stage Filter Vessel Construction: 304 SS

Internal Construction: 304 SS

Piping Material: 304 SS

Reservoir Holding Capacity: Up to 30 gallons (113.56 liters)

Scrubber System Description

The scrubber preferably includes two cylindrical vessels in series. The first tower will contain 3.5' (8.89 cm) of stainless steel packing media with gas flowing upward and water descending for reaction with SO$_3$ and dissolution of H$_2$SO$_4$. The packed tower will utilize a recirculated caustic solution to neutralize the contaminants (chemicals and chemical addition by others.) The second tower will contain one (1) fiberbed filter for the removal of mist earned in the gas stream. The system will include necessary' internal piping, fasteners and other internal appurtenances required for correct operation. The vessels are rated for 1 psi (6.89 kpa) maximum; the scrubber will utilize a pressure regulating valve and expansion chambers to reduce gas pressure within the scrubber.

Scrubber Components and Features:

304 Stainless Steel Vessels

304 Stainless Steel Interconnecting Duct

304 Stainless Steel Pump and Recirculation Piping

Integral Reservoir in each vessel with combined capacity>of 30 gallons (113.56 liters)

304 Stainless Steel Spray Header and Nozzle

Water Connection with Flowmeter and Control Valve

High Efficiency 304 Stainless Steel Packing Media

Differential Pressure Gauges (One (1) per vessel)

1" (2.54 cm) Adjustable Pressure Regulating Valve on Scrubber Inlet

1A" Adjustable Pressure Relief Valves (One (1) per vessel)

Fiberbed Filter with Stainless Steel Mounting Flange

MSSS-10 10 CFM PT Scrubbing System

While exemplary embodiments are described above, it is not intended that these embodiments describe all possible forms of the disclosure. Rather, the words used in the specification are words of description rather than limitation, and it is understood that various changes may be made without departing from the spirit and scope of the disclosure. Additionally, the features of various implementing embodiments may be combined to form further embodiments of the disclosure.

All measurements disclosed herein are at standard temperature and pressure, at sea level on Earth, unless indicated otherwise.

The foregoing embodiments are presented by way of example only; the scope of the present disclosure is to be limited only by the following claims.

What is claimed is:

1. A method of extracting hydrocarbons comprising:
providing a transportable system for on-demand sulfur trioxide generation at or near a well-site of an ice deposit containing a clathrate hydrate, the transportable system having
a portable source of sulfur,
a portable source of oxygen or air containing oxygen, and
a converter fluidly or gaseously coupled to the portable source of sulfur and the portable source of oxygen or air and capable of catalyzing a reaction to generate sulfur trioxide from the sulfur and oxygen, wherein sulfur from the portable source of sulfur and oxygen from the portable source of sulfur are combined to generate sulfur trioxide and the transportable system has dimensions allowing for transport to the well-site;
generating sulfur trioxide with the transportable system;
delivering the sulfur trioxide to the ice deposit where the sulfur trioxide reacts with the clathrate hydrate to generate a hydrocarbon gas; and
recovering the hydrocarbon gas.

2. The method of claim 1, wherein the transportable system generates sulfur trioxide at a rate ranging from about 0.5 (1.89 liters) gallons per hour to about 2000 gallons (7570.82 liters) per hour.

3. The method of claim 1, wherein the hydrocarbon gas is at least one of methane, ethane, butane, propane, or mixtures thereof.

4. The method of claim 1, wherein the sulfur trioxide reacts with the clathrate hydrate to produce a compound of formula (I),

wherein R is linear or branched alkyl group with 1, 2, 3, 4 carbon atoms, or combinations thereof and the method further comprises the step of recovering the compound of formula (I).

5. The method of claim 4 further comprising the step of extracting the linear or branched alkyl group from the compound of formula (I).

* * * * *